(12) United States Patent
Imran et al.

(10) Patent No.: US 8,915,867 B2
(45) Date of Patent: *Dec. 23, 2014

(54) SYSTEM FOR MARKING A LOCATION FOR TREATMENT WITHIN THE GASTROINTESTINAL TRACT

(71) Applicant: Entrack, Inc., Menlo Park, CA (US)

(72) Inventors: Mir Imran, Los Altos Hills, CA (US); Olivier K. Colliou, Los Altos, CA (US); Ted W. Layman, Park City, UT (US); Sharon L. Lake, Menlo Park, CA (US); Harm TenHoff, Mountain View, CA (US); Timothy J. Hughes, Palo Alto, CA (US)

(73) Assignee: Entrack, Inc., Menlo Park, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/010,397

(22) Filed: Aug. 26, 2013

(65) Prior Publication Data
US 2014/0058317 A1    Feb. 27, 2014

Related U.S. Application Data

(63) Continuation of application No. 12/917,446, filed on Nov. 1, 2010, now Pat. No. 8,517,961, which is a continuation of application No. 10/427,672, filed on May 1, 2003, now Pat. No. 7,824,347, which is a continuation of application No. 09/892,404, filed on Jun. 26, 2001, now Pat. No. 7,160,258.

(51) Int. Cl.
*A61B 5/00* (2006.01)

(52) U.S. Cl.
USPC ....................... 600/593; 604/890.1

(58) Field of Classification Search
USPC .................. 600/424, 459, 593; 604/890.1
See application file for complete search history.

(56) References Cited

U.S. PATENT DOCUMENTS

| 3,144,017 A | 8/1964 | Muth |
| 3,229,684 A | 1/1966 | Nagumo et al. |
| 3,403,684 A | 10/1968 | Stiebel et al. |

(Continued)

FOREIGN PATENT DOCUMENTS

| DE | 2929429 | 2/1980 |
| DE | 3440177 | 5/1986 |

(Continued)

OTHER PUBLICATIONS

Andres, M., et al., "Tubeless gastric analysis with a radio-telemetering pill (Heidelberg capsule)," C.M.A. Journal, 102:1087-1089 (1970).

(Continued)

*Primary Examiner* — Max Hindenburg
(74) *Attorney, Agent, or Firm* — Mahamedi Paradice LLP

(57) ABSTRACT

A device and method for mapping, diagnosing and treating the intestinal tract is provided using a capsule passing through the intestinal tract. Further, a capsule tracking system is provided for tracking a capsule's location along the length of an intestinal tract as various treatment and/or sensing modalities are employed. In one variation, an acoustic signal is used to determine the location of the capsule. A map of sensed information may be derived from the pass of a capsule. Capsules may be subsequently passed through to treat the intestinal tract at a determined location along its length. One variation uses an electrical stimulation capsule to treat and/or diagnose a condition in the intestinal tract.

21 Claims, 18 Drawing Sheets

(56) References Cited

U.S. PATENT DOCUMENTS

| | | |
|---|---|---|
| 3,659,600 A | 5/1972 | Merrill |
| 3,672,352 A | 6/1972 | Summers |
| 3,682,160 A | 8/1972 | Murata |
| 3,739,279 A | 6/1973 | Hollis |
| 3,791,377 A | 2/1974 | Norby et al. |
| 3,971,362 A | 7/1976 | Pope et al. |
| 4,239,040 A | 12/1980 | Hosoya et al. |
| 4,278,077 A | 7/1981 | Mizumoto |
| 4,425,117 A | 1/1984 | Hugemann et al. |
| 4,439,197 A | 3/1984 | Honda et al. |
| 4,481,952 A | 11/1984 | Pawelec |
| 4,507,115 A | 3/1985 | Kambara et al. |
| 4,844,076 A | 7/1989 | Lesho et al. |
| 5,024,240 A | 6/1991 | McConnel |
| 5,064,285 A | 11/1991 | Iddan |
| 5,109,870 A | 5/1992 | Silny et al. |
| 5,167,626 A | 12/1992 | Casper et al. |
| 5,170,801 A | 12/1992 | Casper et al. |
| 5,217,449 A | 6/1993 | Yudia et al. |
| 5,279,607 A | 1/1994 | Schentag et al. |
| 5,395,366 A | 3/1995 | D'Andrea et al. |
| 5,415,181 A | 5/1995 | Hogrefe et al. |
| 5,479,935 A | 1/1996 | Essen-Moller |
| 5,515,853 A | 5/1996 | Smith et al. |
| 5,558,640 A | 9/1996 | Pfeiler et al. |
| 5,568,809 A | 10/1996 | Ben-Haim |
| 5,604,531 A | 2/1997 | Iddan et al. |
| 5,681,260 A | 10/1997 | Ueda et al. |
| 5,690,691 A | 11/1997 | Chen et al. |
| 5,694,945 A | 12/1997 | Ben-Haim |
| 5,697,384 A | 12/1997 | Miyawaki et al. |
| 5,792,048 A | 8/1998 | Schaefer |
| 5,800,350 A | 9/1998 | Coppleson et al. |
| 5,808,292 A | 9/1998 | Iddan |
| 5,819,736 A | 10/1998 | Avny et al. |
| 5,833,603 A | 11/1998 | Kovacs et al. |
| 5,836,981 A | 11/1998 | Chang et al. |
| 5,925,030 A | 7/1999 | Gross et al. |
| 5,993,378 A | 11/1999 | Lemelson |
| 6,056,695 A | 5/2000 | Rupp et al. |
| 6,057,909 A | 5/2000 | Yahav et al. |
| 6,091,905 A | 7/2000 | Yahav et al. |
| 6,099,482 A | 8/2000 | Brune et al. |
| 6,170,488 B1 | 1/2001 | Spillman et al. |
| 6,225,901 B1 | 5/2001 | Kail, IV |
| 6,239,724 B1 | 5/2001 | Doron et al. |
| 6,240,312 B1 | 5/2001 | Alfano et al. |
| 6,256,522 B1 | 7/2001 | Schultz |
| 6,285,897 B1 | 9/2001 | Kilcoyne et al. |
| 6,324,418 B1 | 11/2001 | Crowley et al. |
| 6,330,464 B1 | 12/2001 | Colvin et al. |
| 6,428,469 B1 | 8/2002 | Iddan et al. |
| 6,453,199 B1 | 9/2002 | Kobozev |
| 6,475,145 B1 | 11/2002 | Baylor |
| 6,584,348 B2 | 6/2003 | Glukhovsky |
| 6,689,056 B1 | 2/2004 | Kilcoyne et al. |
| 6,711,423 B2 | 3/2004 | Colvin |
| 6,718,210 B1 | 4/2004 | Peckham et al. |
| 6,929,636 B1 | 8/2005 | von Alten |
| 6,950,690 B1 | 9/2005 | Meron et al. |
| 7,037,343 B2 | 5/2006 | Imran |
| 7,039,453 B2 | 5/2006 | Mullick et al. |
| 7,141,071 B2 | 11/2006 | Imran |
| 7,160,258 B2 | 1/2007 | Imran et al. |
| 7,575,550 B1 | 8/2009 | Govari |
| 7,824,347 B2 | 11/2010 | Imran et al. |
| 8,005,536 B2 | 8/2011 | Imran |
| 2001/0035902 A1 | 11/2001 | Iddan et al. |
| 2001/0051766 A1 | 12/2001 | Gazdzinski |
| 2001/0055482 A1 | 12/2001 | Braun et al. |
| 2002/0032366 A1 | 3/2002 | Iddan et al. |
| 2002/0042562 A1 | 4/2002 | Meron et al. |
| 2002/0055734 A1 | 5/2002 | Houzego et al. |
| 2002/0093484 A1 | 7/2002 | Skala et al. |
| 2002/0099310 A1 | 7/2002 | Kimchy et al. |
| 2002/0109774 A1 | 8/2002 | Meron et al. |
| 2002/0111544 A1 | 8/2002 | Iddan |
| 2002/0132226 A1 | 9/2002 | Nair et al. |
| 2002/0146368 A1 | 10/2002 | Meron et al. |
| 2002/0146834 A1 | 10/2002 | Meron et al. |
| 2002/0158976 A1 | 10/2002 | Vni et al. |
| 2002/0165592 A1 | 11/2002 | Glukhovsky |
| 2002/0171669 A1 | 11/2002 | Meron et al. |
| 2002/0173718 A1 | 11/2002 | Frisch et al. |
| 2002/0177779 A1 | 11/2002 | Adler et al. |
| 2002/0185590 A1 | 12/2002 | Yahav et al. |
| 2002/0193669 A1 | 12/2002 | Glukhovsky |
| 2003/0139661 A1 | 7/2003 | Kimchy et al. |
| 2003/0167000 A1 | 9/2003 | Mullick et al. |
| 2004/0068204 A1 | 4/2004 | Imran |
| 2004/0162469 A1 | 8/2004 | Imran |
| 2006/0129237 A1 | 6/2006 | Imran |
| 2007/0093910 A1 | 4/2007 | Imran |
| 2011/0046479 A1 | 2/2011 | Imran |
| 2011/0306897 A1 | 12/2011 | Imran |

FOREIGN PATENT DOCUMENTS

| | | |
|---|---|---|
| DE | 19609564 | 6/1997 |
| EP | 1408820 | 4/2004 |
| FR | 2591095 | 6/1987 |
| FR | 2688997 | 3/1992 |
| JP | 01-193644 | 8/1989 |
| JP | 03-136636 | 6/1991 |
| JP | 04-180736 | 6/1992 |
| JP | 06-137850 | 5/1994 |
| JP | 6089627 | 11/1995 |
| JP | 7289504 | 11/1995 |
| JP | 10-262934 | 10/1998 |
| WO | WO 87/03465 | 6/1987 |
| WO | WO 97/36646 | 9/1997 |
| WO | WO 98/11816 | 3/1998 |
| WO | WO 98/11823 | 3/1998 |
| WO | WO 99/30610 | 5/1999 |
| WO | WO 99/32028 | 7/1999 |
| WO | WO 00/22975 | 4/2000 |
| WO | WO 01/08548 | 2/2001 |
| WO | WO 01/10291 | 2/2001 |
| WO | WO 03/001966 | 1/2003 |
| WO | WO 2004/058101 | 7/2004 |
| WO | WO 2004/058102 | 7/2004 |
| WO | WO 2004/091361 | 10/2004 |
| WO | WO 2005/096937 | 10/2005 |

OTHER PUBLICATIONS

Author Unknown, "Pill-shaped Biotelemetry Transmitters," Sensors 2000.

Carey, L., et al., "Relative electrical impedance as Index to intestinal viability," Archives of Surgery, 89:226-228 (1964).

Cullen, J., et al., "Intestinal pacing," Postsurgical Syndromes, 23(2):391-402 (1994).

Cullen, J., et al., "The future of intestinal pacing," Gastroenterology Clinics of North America, 23(2):391-402 (1994).

d'Haens, J., et al., "The endomotorsonde, a new device for studying the gastrointestinal tract," The American Journal of Medical Electronics, Jul.-Sep. issue, pp. 158-161 (1964).

Eagon, J., et al., "Gastrointestinal pacing," Surgical Clinics of North America, 73(6):1161-1172 (Dec. 1993).

Gastrotarget Corporation, "Technology and Company Perspective," pp. 1-13, Mar. 27, 2000.

Gong, F., et al., "Wireless endoscopy," Gastrointest. Endosc., 51(6):725 (2000).

Lambert, A., et al., "Autonomous telemetric capsule to explore the small bowel," Medical & Biological engineering & Computing, March Issue, pp. 191-196 (1991).

Otterson, M., et al. "Normal physiology of small intestine motility," Surgical Clinics of North America, 73(6): 1173-1192 (1993).

Vaxman, F., et al., "Small bowel biopsy by remote control," Digestive Deseases and Sciences, 41(2):295-300 (1996).

Dec. 15, 2009 Official Decision of Refusal in Japanese Application No. 2003-508213.

(56) References Cited

OTHER PUBLICATIONS

May 19, 2009 Notification of Reason(s) for Refusal in Japanese Application No. 2003-508213.
Non-Final Office Action mailed Nov. 28, 2011 in U.S. Appl. No. 12/917,446.
Final Office Action mailed Jun. 11, 2012 in U.S. Appl. No. 12/917,446.
Non-Final Office Action mailed May 10, 2012 in U.S. Appl. No. 13/215,182.
Non-Final Office Action mailed Apr. 24, 2006 in U.S. Appl. No. 10/745,439.
Non-Final Office Action mailed Jan. 9, 2007 in U.S. Appl. No. 10/745,439.
Final Office Action mailed Sep. 20, 2007 in U.S. Appl. No. 10/745,439.
Non-Final Office Action mailed Jun. 6, 2008 in U.S. Appl. No. 10/745,439.
Final Office Action mailed Mar. 19, 2009 in U.S. Appl. No. 10/745,439.
Non-Final Office Action mailed Dec. 1, 2009 in U.S. Appl. No. 10/745,439.
Final Office Action mailed Aug. 18, 2010 in U.S. Appl. No. 10/745,439.
Non-Final Office Action mailed Sep. 2, 2011 in U.S. Appl. No. 10/745,439.
Non-Final Office Action mailed Mar. 29, 2013 in U.S. Appl. No. 13/752,357.
Non-Final Office Action mailed Apr. 16, 2013 in U.S. Appl. No. 13/215,182.
Notice of Allowance mailed Apr. 29, 2013 in U.S. Appl. No. 12/917,446.
Non-Final Office Action mailed Jan. 3, 2014 in U.S. Appl. No. 13/215,182.

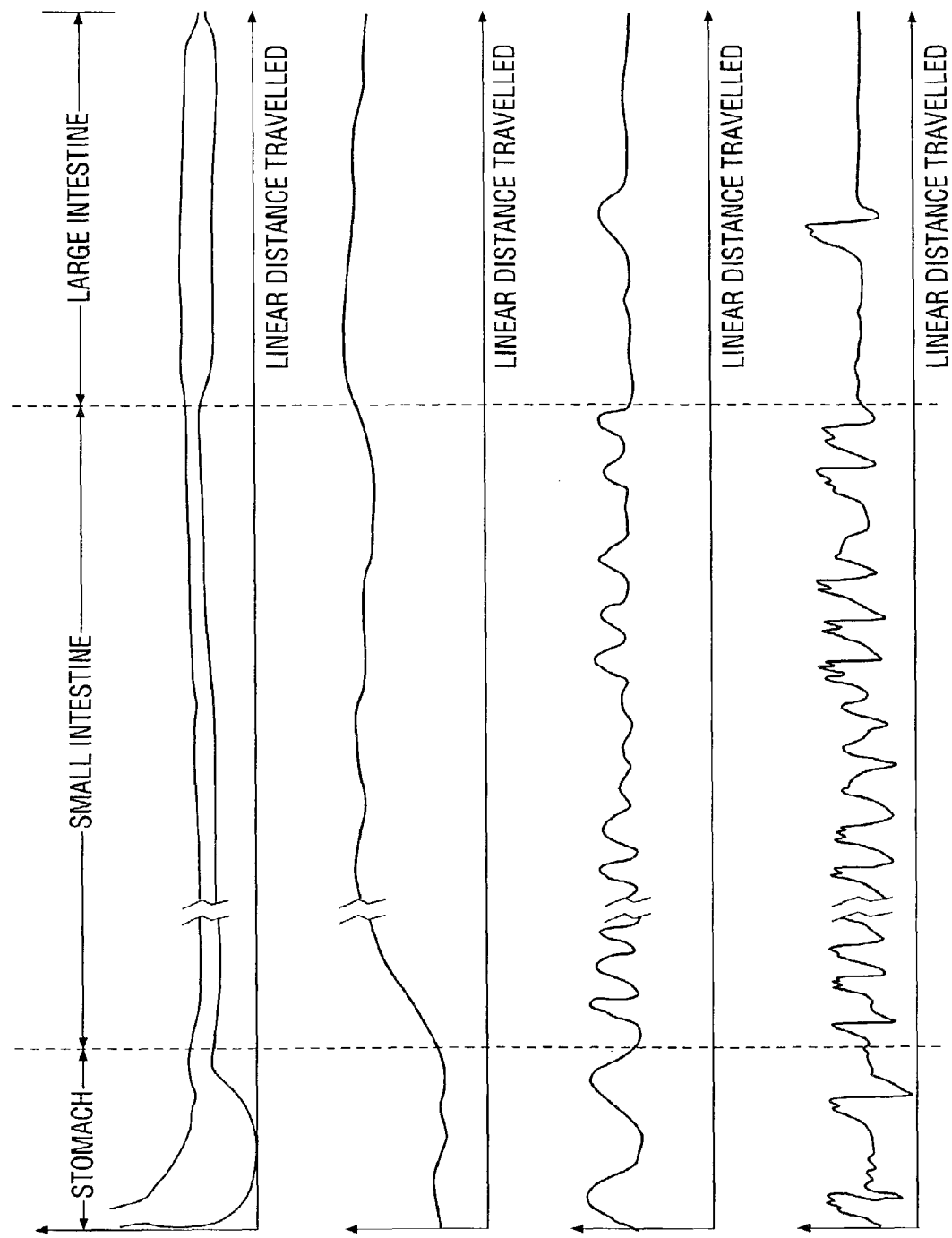

SYSTEM FOR MARKING A LOCATION FOR TREATMENT WITHIN THE GASTROINTESTINAL TRACT

RELATED APPLICATIONS

This application is a continuation of U.S. application Ser. No. 12/917,446 filed Nov. 1, 2010 and issued as U.S. Pat. No. 8,517,961 on Aug. 27, 2013 which is a continuation of U.S. application Ser. No. 10/427,672 filed May 1, 2003 and issued as U.S. Pat. No. 7,824,347 on Nov. 2, 2010 which is a continuation of U.S. application Ser. No. 09/892,404 filed Jun. 26, 2001 and issued as U.S. Pat. No. 7,160,258 on Jan. 9, 2007; all of the aforementioned priority applications are hereby incorporated herein by reference in their entirety.

FIELD OF THE INVENTION

This invention relates to a device and method for mapping, diagnosing and treating the intestinal tract using a capsule passing through the intestinal tract. Further, this invention relates to a capsule tracking system for tracking a capsule's location, including for tracking a corresponding diagnosis or treatment, along the length of an intestinal tract. The invention also relates to various treatment and diagnosis methods and devices that may be used with such a capsule and in such a tracking system. One of such devices and methods concerns influencing and/or measuring the electrical behavior of the intestinal tract.

BACKGROUND OF THE INVENTION

Different areas of the intestinal tract have varying degrees of surgical accessibility. For example, there has been great difficulty in diagnosing and treating disorders in the human small intestine because of the length of the small intestine (typically about 21 feet or 7 meters), and its inaccessibility. Also certain regions of the colon have proven difficult to access for treatment. Accordingly, it would be desirable to provide a less or minimally invasive device for diagnosing or treating difficult to access portions of the intestinal tract, such as, the small intestine and colon.

Swallowable telemetry capsules have been used in a number of treatment and diagnostic applications. Some swallowable capsules have been proposed to deliver medication to specific areas of the intestinal tract where the release of the medication is actuated by an external RF signal received by the capsule. The signal actuates an electromechanical device within the capsule to release the medication. Similarly, some capsules have been proposed to acquire samples from the intestinal tract where actuation of an electromechanical sampling device is remotely controlled and the capsule is then retrieved when excreted. Other capsules have been proposed, for example, to take pictures or video images, or measure pH, pressure or temperature. An autonomous capsule with electrodes has been proposed to provide electrical stimulation while moving through the GI tract to restore motor evacutory function of the GI tract. Such a device has been proposed to propel a capsule through the gut.

Telemetry treatment and/or diagnostic capsules with mapping capabilities have been proposed to identify a target treatment site on a three-dimensional map of the intestinal tract. Generally, the proposed systems include capsules that transmit RF signals to externally located antennas. The relative amplitudes of the RF signals received by the antennas are used to determine relative location of the capsule based on the correlation between the capsule to antenna distance and RF amplitude (signal strength). According to these proposed systems, using four or more antennas and triangulation techniques, the location of the capsule in two or three-dimensional space is determined based on RF amplitude. From the location information, a map of the capsule's path in space may be created. In subsequent passes of the capsule through the intestinal tract, the capsule is used for treatment or diagnosis purposes at a target location. In addition, it has been proposed to use video images in combination with such RF determined spatial information to identify a target location in first and subsequent capsule passes.

A capsule with a mechanical cogwheel has been proposed to calculate the small bowel length and small bowel transit velocity. The device relies on the turning of the cogwheel by contact with the intestinal wall during small bowel transit to calculate centimeters of travel.

Many disadvantages are inherent in the current capsule tracking techniques. Tracking systems using RF amplitude data from signals transmitted through body tissue have a high degree of error and inadequate resolution for accurate intestinal tract mapping. (With 1 cm intestinal diameters and substantial overlap of intestines, an accurate resolution is necessary.) The resolution problems are due to a number of possible inaccuracies, which are compounded because RF signal strength over distance varies in a non-linear fashion. RF signal is directional, and thus its strength varies with the direction of the signal or the orientation of the coil transmitter with respect to the fixed coil receiver. Thus, without any change in location, a change in orientation may cause a dramatic change in RF amplitude at the antenna. Further, RF transmission is absorbed by tissue, particularly at higher frequencies. Thus the larger coils that would be required to transmit lower frequency RF signals, constrain the ability to miniaturize an optimal device.

In addition to RF resolution issues, due to movement and shifting of the intestinal organs within the abdomen, 3D mapping may not repeatably identify a precise location within the intestines when a subsequent capsule is passed through the tract. The intestinal organs tend to shift with the filling or emptying of the various portions of the digestive system, and they tend to move with peristalsis. A patient's abdomen also moves with respiration and change in patient position. Thus, given the intestinal shifting along with the intestine's small diameter and overlap, the 3D tracking system may identify the wrong portion of the intestinal tract when a later capsule passes through. Therefore, it would be desirable to provide a tracking system that accurately and repeatably identifies a desired location in the intestinal tract so that a location identified by a first capsule is substantially the same as a location identified by a subsequently passed capsule. It would also be desirable to provide a capsule and tracking system that does not rely on RF transmission amplitude data for accurate tracking.

As noted above, telemetry capsules have been used in therapeutic and diagnostic applications. Such therapeutic and diagnostic devices have typically involved providing medication to a location in the intestinal tract alone or in combination with sampling the fluids of the intestinal tract. The pH, temperature and pressure have also been measured. It would be desirable to provide capsules with new diagnostic and treatment modalities, particularly in a manner that would combine the treatment with tracking and diagnostic capabilities, to treat difficult to access regions of the intestinal tract.

One clinically significant condition that has been challenging to treat in the intestines is bleeding. Location of bleeding in the intestinal tract is very difficult to identify and requires surgical intervention to correct if it persists. Therefore, it would be desirable to provide a method and device for identifying a location of intestinal bleeding and for treating the location in a less invasive manner.

Another diagnostic/therapeutic area of interest is in identifying blockages or other diseased portions of the intestine and the ability to biopsy the specific location where there is such a blockage or disease. It would also be of interest to assist a surgeon in specifically marking a site for surgery prior to surgical intervention for easier identification of the site.

Another clinically significant parameter is the transit time of materials through the intestines. Current techniques in measuring transit time involve ingesting a material that reacts with the contents of the colon such that the patient's breath gives off a detectable gas at such time. This technique is not very precise and does not provide information on, e.g., which particular portion of the tract is responsible for transit abnormalities. Some patients have segmental diseases where a segment of the intestine does not have adequate motility. Thus, velocity of travel of materials through various portions of the intestine would be of interest in determining where there may be segmental disease.

Motility disorders in some situations relate to abnormalities in the periodic, coordinated contractile activity of the smooth muscles associated with the intestinal tract. Various organs of the intestinal tract such as the stomach, small intestine and colon contain cells that are believed to govern the organs' periodic contractile behavior. In healthy humans, in certain intestinal tract regions, these cells generate and propagate rhythmic electrical signals. In general, several types of electrical potential activities have been observed in the intestinal tract. Consistent slow wave or pacesetter potentials have been observed and higher frequency spike activity has been observed. The pacesetter potentials are continuously propagating, relatively low frequency, cyclic depolarizations of the smooth muscle lining. The higher frequency spike bursts tend to correspond with smooth muscle contractile activity including segmentation and peristalsis. In general, when the spike burst activity occurs, it appears to be at a fixed time delay with respect to the slow wave potentials. It is believed that when the pacesetter potentials are combined with a chemical or neural excitation of the cells, smooth muscle contractile activity may occur and that the pacesetter potentials control and coordinate the frequency and direction of the contractions.

Accordingly, it would be of interest to provide a means for observing the electrical activity such as, for example, the vagal nerve activity, the electromyogram, or of the intestinal smooth muscle layers, etc., to determine whether the electrical activity is abnormal, indicating possible disease.

Electrical stimulation of the gastrointestinal tract has been proposed to treat motility related disorders and other gastrointestinal diseases. The electrical stimulation has been proposed in a number of forms, such as, e.g., pacing; electrical contractile stimulation or other stimulation; e.g., to treat nausea. Electrical pacing of the intestinal tract is generally defined as periodic electrical stimulation that captures and/or controls the frequency of the pacesetter potential or slow wave activity of the intestinal organ (including in a retrograde direction). Electrical contractile stimulation generally refers to stimulation that directly causes or results in muscular contraction associated with the intestinal tract.

In some disease states, dysrhythmias of the intestinal tract pacesetter potentials may be present. Electrical pacing of pacesetter potentials has been proposed to induce regular rhythms for the pacesetter potentials with the intent of inducing regular or controlled intestinal tract contractions. Pacing has also been suggested to cause retrograde propagation of pacesetter potentials. Also, electrical contractile stimulation of the intestinal tract has been proposed to induce peristalsis.

Many currently proposed intestinal tract electrical stimulation procedures are relatively invasive and require accessing the intestinal tract through the abdomen, e.g., in an open or a laparoscopic procedure. The devices used typically require implanting permanent leads, electrodes and a pacemaker within the body. Therefore, it would be desirable to provide a less invasive device for electrically stimulating the intestinal tract, particularly in combination with a system for tracking the device and delivering the treatment to an identified location.

SUMMARY OF THE INVENTION

The present invention provides a capsule having diagnostic and/or treatment capabilities, and a system for tracking the capsule through the intestinal tract. One embodiment of a tracking system provides an improved system for determining the coordinates of a capsule in three-dimensional space. According to this embodiment, an acoustic signal is transmitted between a capsule as it is passing through the intestinal tract, and a location external a patient's body. As such an acoustic transmitter or transmitters are located either at the capsule or location external to the patient's body and the acoustic receiver(s) or sensor(s) are located at the other of either the capsule or location external a patient's body. The velocity of an acoustic signal through tissue is predictable (ultrasound transmits through tissue at about 1540 meters per second). Using the amount of time the signal takes to travel to the receiver(s) and the signal velocity, the relative capsule distance(s) to the location(s) external the patient's body is determined. Also, it should be noted that the transit time of the acoustic signal is linearly proportional to the distance traveled.

In one preferred embodiment, a capsule passing through the intestinal tract transmits an acoustic signal through the body to a plurality of externally located acoustic sensors. The relative capsule distances to the sensors are determined using the amount of time the signal takes to travel to the receiver. Triangulation of the comparative distances will result in a location of the capsule in space (for example, on a Cartesian coordinate system).

According to a preferred embodiment, a reference signal is used to identify the time of acoustic signal origination. In one variation, reference signal may be in the form of an RF reference signal delivered from the capsule to an external sensor where the capsule emits the acoustic signal. In this variation, the RF reference signal is delivered at predetermined time from the emission of the acoustic signal. The RF signal, which travels at the speed of light, is received by the sensors relatively instantaneously. The RF signal is used by the sensor/receiver to determine when the acoustic signal was transmitted. Alternatively, in another variation, an external, telemetrically delivered electromagnetic control signal may be used to trigger the emission of the acoustic signal from the capsule, thereby providing a time reference. Where the acoustic transmitter is at located externally of the patient, the reference signal, for example, may also be a trigger signal that triggers emission of the acoustic signal from and external transducer. In various other embodiments, the reference signal may utilize other communication media to provide a reference signal. For example, an infra-red link or a distributed resistive link could be used. According to these alternative embodiments, signals may be transmitted either to or from the capsule.

Another embodiment provides a tracking system that tracks a capsule's linear position along the intestinal tract length or a portion thereof. As the capsule moves through the tract, it senses diagnostic information. The tracking system correlates sensed diagnostic information with the capsule's corresponding linear position when the information is sensed. From the diagnostic information, a location along the length traveled is identified for treatment or therapeutic functions, which also include acting on the intestinal tract for a therapeutic purpose, e.g., to mark the location for surgical intervention. A location along the length may also be identified for further diagnosis, including using subsequently passed capsules.

In a subsequent pass of a capsule, the capsule's linear position is monitored until it reaches the position along the length identified by a previous capsule. At that location, the subsequent capsule then provides, treatment, further diagnosis, or marking. Because the intestinal tract length is relatively constant, the tracking system provides a means for locating a portion of the intestinal tract that is relatively independent of intestinal tract shifting or movement. Thus, the system also provides repeatable tracking independent of the location of the sensors or pods on the patient. The system of this embodiment thus allows for subsequent passes of the capsule where the sensors or pods have been repositioned, for example in a later treatment cycle. In a preferred embodiment, the sensors are provided with the ability to actively locate each other in a three dimensional coordinate system. This allows the sensors to re-calibrate to determine their relative location when they have moved due to respiration, or other patient movement. Because the location of the capsule in a preferred embodiment of the tracking system depends on the relative location of the sensors, re-establishing the relative sensor location on a regular basis compensates for sensor movement during a procedure using tracking.

Preferably, the position of a capsule along a length of the intestinal tract is determined by first identifying the capsule's 3-dimensional position over time, for example, on a Cartesian coordinate system created by the pods. The tracking system includes a processor that monitors the signals from the pods and that uses incremental change in position over time to convert the 3D capsule location information to linear travel distance measurements. The linear travel distance measurements are then used to derive the capsule's position along the length of the intestinal tract portion of interest. Preferably the tracking system uses acoustic transmission time from the capsule to external sensors to determine the capsules 3D coordinates as described herein. An initial location of the capsule is preferably first identified, such as, when it reaches the pylorus. Such position may be determined by a number of means such as by determining capsule movement indicative that the capsule is moving from the stomach into the small intestine, including, for example change in location, or acceleration. Alternatively a capsule's initial location may be determined, for example by pressure, which changes when the capsule passes through the pylorus, or pH, which changes when the capsule enters the duodenum.

Another feature of the invention provides a system to compensate for variations in capsule location determinations along the length of the intestinal tract that are due to intestinal smooth muscle contractions and corresponding foreshortening of the intestinal tract. For example, pressure may be measured to determine the relative relaxation/contraction of the tract and the corresponding foreshortening. The determination of capsule location may be a factor of such pressure. Another feature of the invention provides a filter that detects and filters out capsule movement not corresponding to actual movement along the length of the tract. For example, by observing the orientation and type of movement, movement that is not statistically related to movement along the intestinal length may be filtered out.

Another feature of the invention is a capsule having a plurality of acoustic transducers to provide information concerning directional orientation of the capsule.

Although the linear tracking system may not require sensing of additional parameters to determine location, the linear tracking is used as a diagnostic tool when combined with other sensed information to provide a diagnostic linear map of the intestinal tract or a portion thereof (such as the small intestine.) Further, the tracking system is preferably combined with both diagnostic and treatment functions. In use, after a diagnostic capsule provides a diagnostic linear map of the intestinal tract, a treatment capsule is passed through intestinal tract portion. The treatment capsule that travels through the intestinal tract is monitored by the tracking system for its relative linear position until it reaches a position along the intestinal tract length to be treated. The mechanism for providing the treatment is then actuated, typically by a telemetrically delivered control signal.

A number of capsules may be used as a combined diagnostic and treatment system. For example, a first capsule obtains information on the capsule position along the intestinal length and corresponding diagnostic information (if desired, a diagnostic linear map of the tract). Another capsule may then be passed through the tract to provide treatment and/or diagnosis at a desired location along the length of the tract. Once the length of the tract has been mapped, any number of subsequent capsules may be passed through to further obtain diagnostic information or to provide treatment. Using this technique a clear map of diagnostic information vs. length of intestine may be obtained. Additional capsules may be used at a later time using the same map for additional diagnosis, treatment or follow up. Also a combination of capsules may be swallowed in a spaced apart sequence where more than one capsule is in the digestive system at one time.

A diagnostic capsule may sense a number of parameters such as, for example, pH for assessing acidity levels in the intestinal tract, electrical activity, electrical impedance, optical parameters for detection of specific reflected or transmitted light spectra, e.g. blood, objects or obstructions in the intestinal tract, pressure for intestinal tract manometric data acquisition and various diagnostic purposes such as determining effectiveness of stimulation, blockages or constrictions, etc., etc. An acoustic transducer, for example, piezoelectric crystals, may be used for performing diagnostic ultrasound imaging of the intestinal tract etc. Also, a temperature transducer may be used. Also, from the positional information over time, capsule transit time, velocity, and acceleration may be calculated and used to identify locations or segments of the intestine where there are motility disorders (such as segmental diseases).

A treatment capsule with the described tracking system subsequently passing through the identified portion to be treated will be signaled to provide treatment. The treatment capsule may include but does not require any diagnostic sensors. The treatment capsules may perform one or more of a number of treatment functions. Such treatment may take several forms or combinations that may include, for example, delivering an electrically stimulating signal, treating bleeding with ablation, clotting agents or coagulants, active or passive drug delivery or gene therapy treatment at specific portions of the tract, an inflatable element for performing balloon plasty of the intestinal tract, for placing a stent (e.g. for strictures), a self expanding stent delivery system, tissue biopsy or content sampling devices, or marking devices, (e.g. staining, marking or tattooing ink, such as india ink, methylene blue or purified carbon powder; radiopaque dye; or magnetic devices) e.g., for locating a portion of the tract for surgery, etc.

One embodiment of the capsule system includes a sensor for detecting the presence of blood. For example, an optical sensor or a chemical sensor may be provided that senses the presence of blood. The capsule is passed through the intestine and the location of the capsule along the length of the tract where the blood is sensed is identified. A treatment capsule having bipolar electrodes is then passed through the intestinal tract until it reaches the identified length of the tract where bleeding is occurring. An external power source is coupled to an RF coil within the capsule to deliver a current through the electrodes to ablate or cauterize the bleeding tissue. Alternatively, a site where bleeding is present may be treated using a subsequently passed capsule having a balloon tamponade, i.e. an inflatable member that uses compression and/or a thrombogenic substance coated on the inflatable member to help cause hemostasis.

Another embodiment of the capsule system comprises a diagnostic capsule that includes a sensor (such as a pressure sensor) that identifies a blockage, stricture or narrowing of the intestine. The location of the capsule along the length of the intestine is tracked. The sensed blockage is correlated to the capsules linear position along the intestinal tract. The tracking system tracks the linear position of a treatment capsule as it passes through the tract until it reaches the location of the blockage. An externally transmitted telemetric signal causes a balloon plasty capsule to deploy an expandable member that dilates the intestinal passage. In one variation, a variable size balloon may be used to determine the extent of a blockage. In this variation, for example, a balloon may be inflated at the suspected blockage area. The balloon is gradually deflated until it passes through the blocked area. The diameter of the balloon when the balloon is able to pass through the constricted site may, e.g., be used to determine extent of the blockage. The diameter of the balloon may be approximated from the volume of inflation medium in the balloon. In another variation a balloon may be provided with an expandable support structure over the balloon such as a stent. The stent may be deployed within the intestinal tract when the balloon is expanded and thereby provide additional radial support of the intestinal wall.

Another embodiment of the capsule system provides a diagnostic capsule for which position and corresponding diagnostic information are tracked along the length of the intestinal tract. A location for surgical intervention is identified based on the diagnostic information and a second capsule is passed through the tract. When the second capsule reaches the linear position of the location for surgical intervention, a telemetric signal is delivered from an external device that triggers the release of a marker within the tract at the desired location. Such marker may include, for example a radiopaque marker that may be located with an x-ray system during a procedure, a fluorescing compound that is used to identify the location (e.g., fluorescein), or a dye that stains through the wall of the intestine (e.g. staining, marking or tattooing ink, such as india ink, methylene blue or purified carbon powder, radiopaque dye). The markers may assist a surgeon in a laparoscopic or open procedure where such imaging systems are used during the procedure or where visualization is possible, e.g. of a stain.

In an alternative embodiment, a capsule may be used to mark a location in the intestinal tract by affixing itself to the intestinal wall at an identified location. Such capsule may include deployable anchor mechanisms where an actuation mechanism causes the anchor to deploy. For example, an external telemetric command signal may trigger the release of such anchor. Such anchor may be provided in a number of forms including an expandable member, or other wall engaging mechanism. The capsule may also be provided with a light emission source such as a laser or an IR source, that emits light to enable location of the capsule, preferably when the capsule is affixed to the intestinal wall.

Another embodiment of the treatment capsule system is an ingestible capsule that will electrically stimulate a predetermined portion of the intestinal tract. Electrical stimulation is generally defined herein to mean any application of an electrical signal or of an electromagnetic field to tissue of the intestinal tract for a therapeutic purpose or to obtain diagnostic information. According to this embodiment, electrical signals are delivered to intestinal tract tissue by at least one electrode, preferably a bipolar electrode pair, or one or more selected electrode pairs coupled to the capsule that electrically stimulates the intestinal tract as the capsule passes through it.

The electrodes deliver a signal that is designed to cause desired therapeutic effect, for example, a smooth muscle response, i.e., stimulation or inhibition of contraction or peristaltic motion. The electrodes may deliver the electrical stimulation to the smooth muscle by contacting, for example, the tissue that forms the intestinal lining or the mucosal tissue of the intestinal tract.

In one preferred treatment method, the electrical stimulation signal entrains a slow wave signal of a portion of the intestinal tract smooth muscle that is clinically absent, weak, of an undesirable frequency, sporadic or otherwise not optimal. Also, the capsule may transmit other electric stimuli. In one embodiment the electrical stimulus is designed to trigger the spike burst electrical activity of the smooth muscle associated with smooth muscle contractions. The stimulating signals may also be designed to inhibit the inherent smooth muscle pacing potentials, to reduce smooth muscle contractions. The signals may also be designed to disrupt the natural waveform and effectively alter the existing or inherent pacing.

The stimulation electrodes provide stimulation either by way of a preprogrammed generator or one that is programmed while the capsule is in the intestine, e.g., based on sensed parameters or response to stimulation. In one embodiment, the capsule acts as a slave to an external device providing master stimulation signals that are received by the capsule and delivered to the tissue.

The stimulation capsule of the present invention may include a plurality of electrodes that may be utilized for forward or backward electrical stimulation, e.g., where the order in which a series of electrode pairs are activated can cause peristalsis to move in a directional manner. A plurality of electrode or bipolar electrode pairs may be provided. Such electrodes, electrode pairs or combination of electrodes or electrode pairs may be selected for delivering stimulation pulses, (either preprogrammed or programmed while the electrodes are deployed in the intestine) to optimize various parameters, e.g. impedance, current density, optimal tissue contact, etc.

The capsule is swallowed or alternatively delivered endoscopically to a predetermined portion of the intestinal tract. The capsule is sized and has a conformity such that it can then readily pass through the intestinal tract. For example, the capsule may pass from the stomach to the small intestine to the colon and exit from the intestinal tract through a bowel movement, permitting its recovery if desired. Also, the capsule may, in general, move with the food material as it passes through the intestinal tract.

The capsule is preferably provided with RF or other signal transmission capabilities, e.g., light. The signal transmission may be used in a number of manners. As described above, the system may have RF signal transmission capabilities that enable determination of a location of the capsule by providing a reference for the time of the acoustic signal initiation.

The signal transmission capabilities may also be used for telemetric communication between the capsule and an external device, e.g., to communicate data to the external device or to receive additional capsule programming information, command signals, or stimulation signals from the external device.

The capsule may be used to sense electrical parameters. For example the capsule electrodes can be used to sense native pacesetter potential (slow wave activity) as well as spike burst activity which corresponds to muscular contractions. The electrodes may also be used to determine tissue impedance. By recording the electrically sensed signals and combining that information with tracking information a comprehensive knowledge of the electrical behavior of the intestinal tract can be gained. Information such as absence of slow wave activity, slow wave frequency, presence of spike burst activity, number of spike burst events per slow wave, and spike burst frequency can assist the clinician in detection and pinpoint location of various disorders such as intestinal neuropathy, tachyarrhythmia, ileus, etc. Preferably the electrical characteristics are correlated to the capsule's movement along the length of the tract to provide a diagnostic linear map of the intestinal tract.

A number of capsules may be passed through in series so that the capsules follow each other in short spaced time intervals. A first capsule provides diagnostic information correlated to the capsule's position along the length of the intestine. A subsequent capsule may provide electrical stimulation based on the sensed conditions. A number of capsules may be passed through, each time obtaining diagnostic information or providing treatment according to the linear map.

The electrical stimulation capsule may be provided with one or more sensors for sensing various conditions in the intestinal tract. Also, the information obtained by the sensors may by communicated via telemetry to a control or locating device that evaluates the sensed information and sends a control signal to the capsule in response, instructing the capsule to perform a particular function or may provide such stimulation signals to the capsule to be delivered through the electrodes on the capsule. The capsule may combine the electrical stimulation feature with other therapeutic or diagnostic capsule functions such as, for example, drug delivery, biopsy or other material sample recovery, etc. Finally, the sensed parameter may be used to ascertain whether or not the stimulated portion is contracting in response to electrical stimuli received from the capsule. For example, the pressure or change in pressure within the tract at a particular location may be indicative of a contractive response to electrical stimulation.

As an alternative to relying on the tracking system described herein, an electrical stimulation capsule may respond to the sensed information by performing a function, such as, for example, by initiating, altering or ceasing delivery of stimulation signals upon sensing of electrical activity, pressure or pH conditions that identify the location of the capsule or condition of the intestinal tract at the location.

In a variation, the inventive capsule includes an encasing at least a portion of which is dissolvable in fluids in the intestinal tract. The encasing may selectively dissolve depending on the pH of the tract. For example, the encasing may dissolve in the small intestine where the pH is substantially neutral in comparison to the acidic stomach conditions. Dissolving the encasing may release a component contained within the capsule for example, so that encased electrodes are exposed or deployed at a desired location.

Another feature of the invention is a capsule having the capability of functioning regardless of the directional orientation in the intestinal tract.

In a preferred embodiment, the capsule and method described above are used in stimulating the small intestine. One variation of this embodiment provides for small intestine pacing.

Additional features of the invention will appear from the following description in which the preferred embodiments are set forth in detail in conjunction with the accompanying drawings.

DETAILED DESCRIPTION OF THE DRAWINGS

FIGS. 8A-G illustrate a timing diagram of signal emission and reception of an exemplary tracking system of the present invention.

Figure 8A:

FIG. 8A illustrates the emission of the RF reference signal.

Figure 8B:

FIG. 8B illustrates the emission of an ultrasound signal from the capsule.

Figure 8C:

FIG. 8C illustrates the timing of the reception of the RF reference signal by the Pods.

Figure 8D:
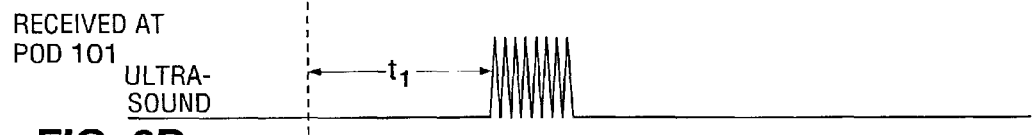

FIG. 8D illustrates the timing of the reception of the ultrasonic signal at the first Pod.

Figure 8E:
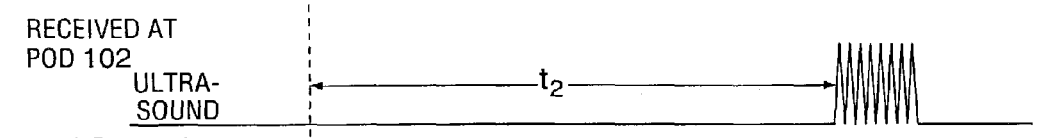

FIG. 8E illustrates the timing of the reception of the ultrasonic signal at the second Pod.

Figure 8F:
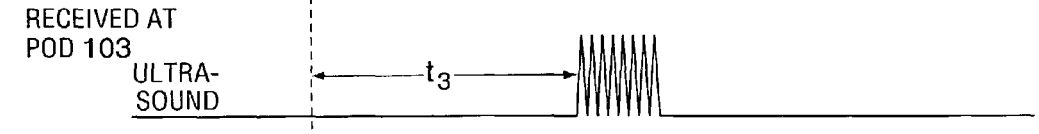

FIG. 8F illustrates the timing of the reception of the ultrasonic signal at the third Pod.

Figure 8G:
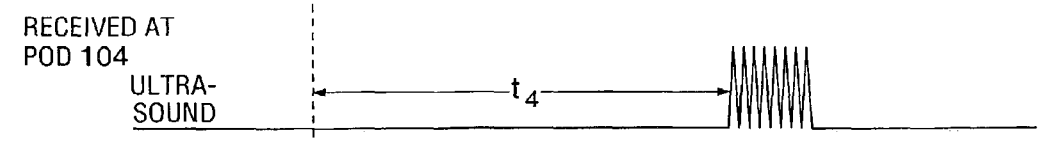

FIG. 8G illustrates the timing of the reception of the ultrasonic signal at the fourth Pod.

Figure 9:
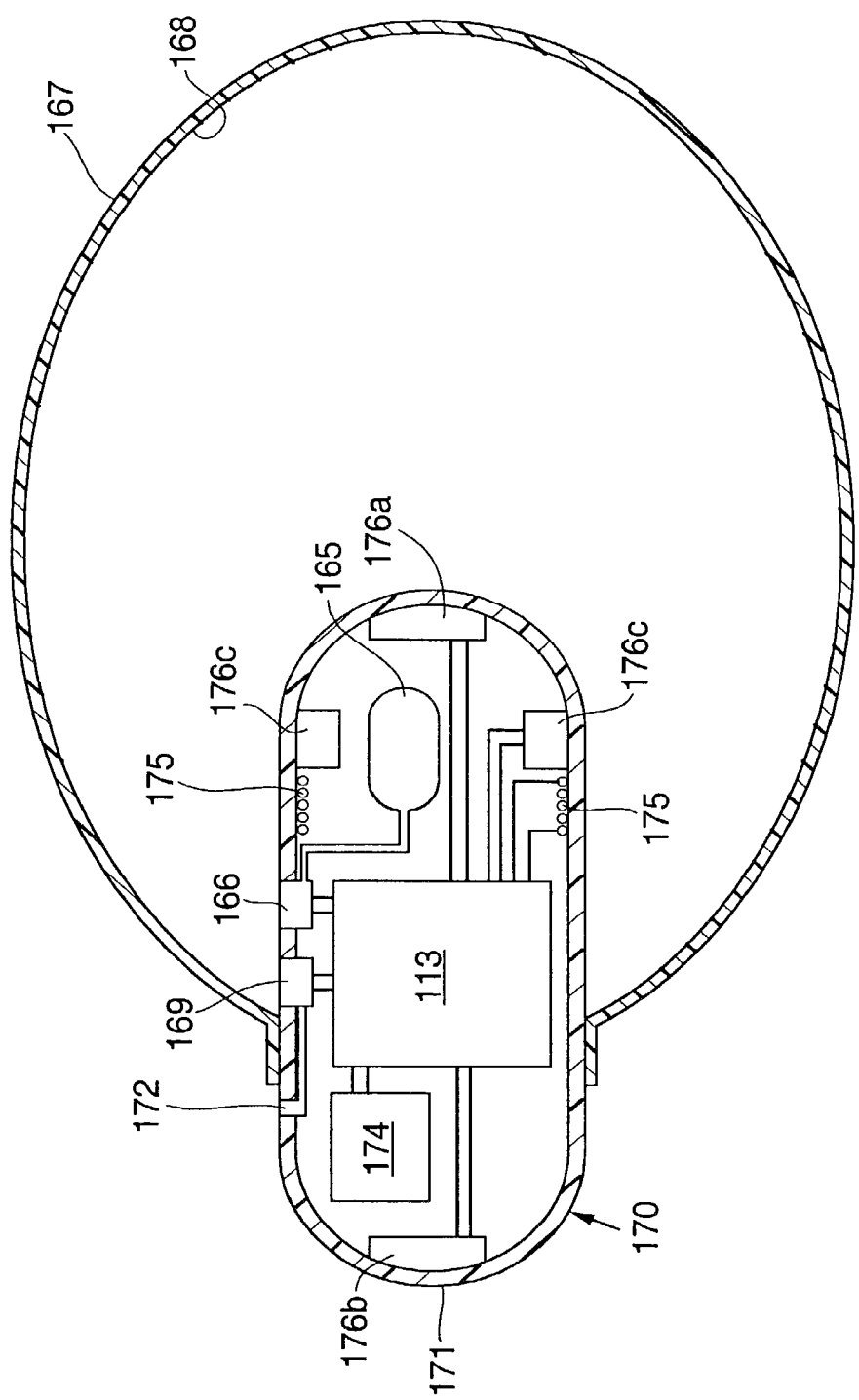

FIG. 9 illustrates a partial cross-sectional view of a second embodiment of a capsule of the present invention.

Figure 10:
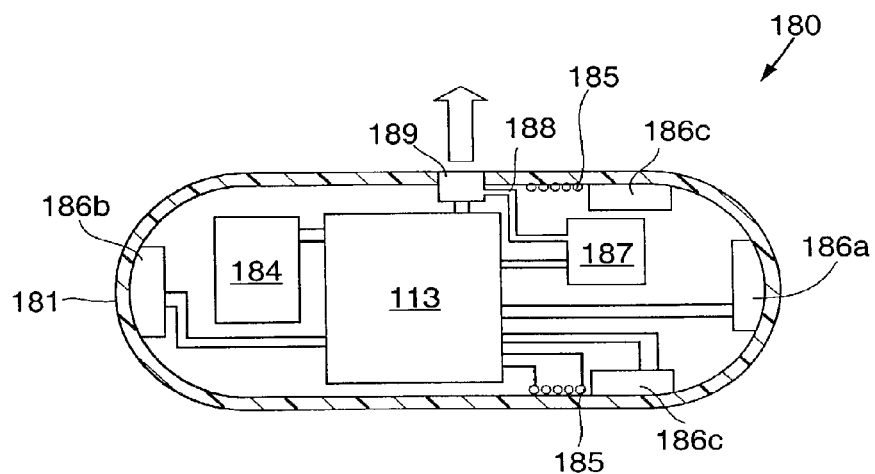

FIG. 10 illustrates a partial cross-sectional view of a third embodiment of a capsule of the present invention.

FIG. 11A illustrates an example of the length of a gastrointestinal system.

FIG. 11B illustrates an example of a map of pH as sensed in relation to the linear position of a capsule along the length of the tract of FIG. 11A.

FIG. 11C illustrates an example of a map of pressure as sensed in relation to the linear position of a capsule along the length of the tract of FIG. 11A.

FIG. 11D illustrates an example of a map of electrical activity as sensed in relation to the linear position of a capsule along the length of the tract of FIG. 11A.

Figure 12:
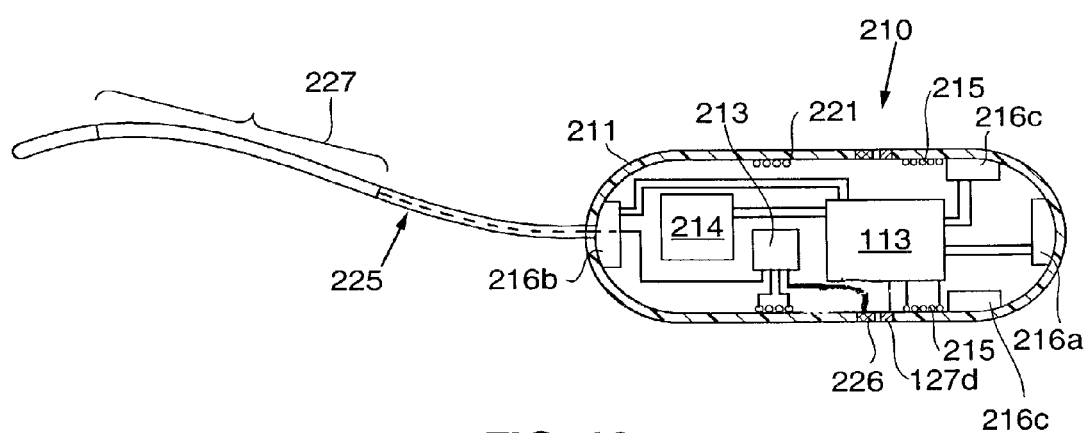

FIG. 12 illustrates a partial cross-sectional view of a fourth embodiment of a capsule of the present invention.

Figure 13:
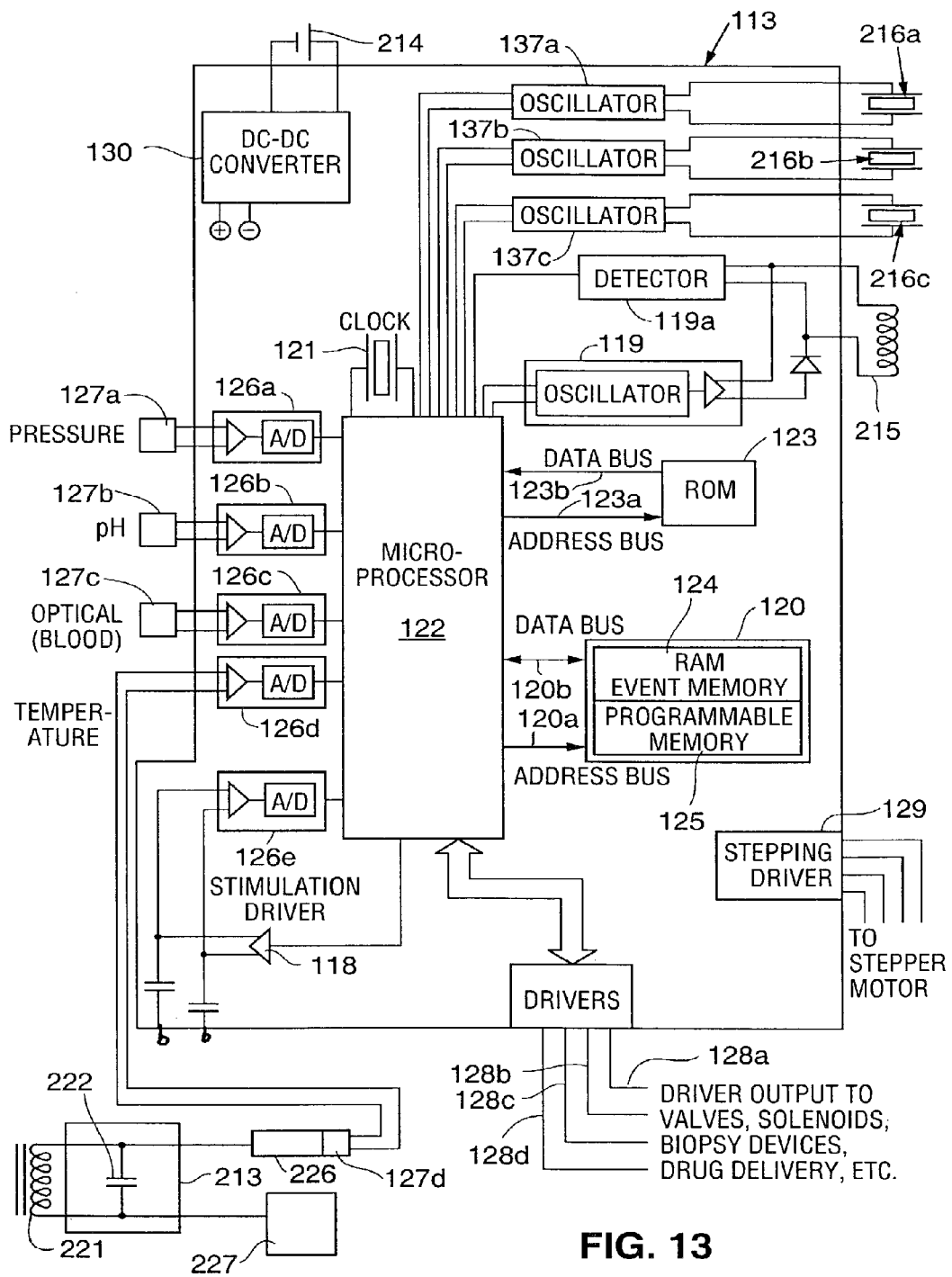

FIG. 13 illustrates the electronic circuitry for the capsule of FIG. 12, including ablation electronics.

Figure 14:
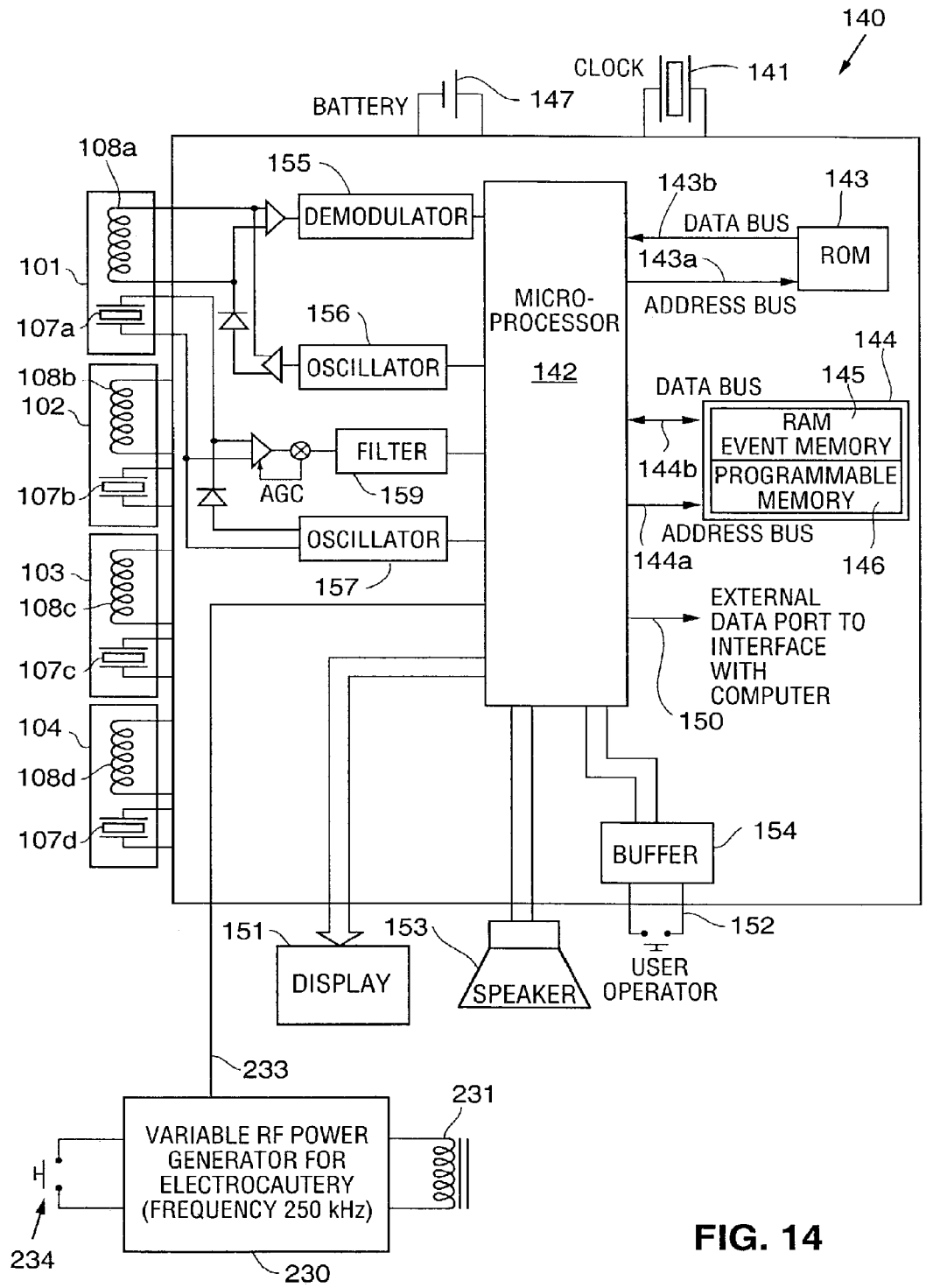

FIG. 14 illustrates the electronic circuitry for an external power source for the ablation function of the capsule of FIG. 12.

Figure 15:
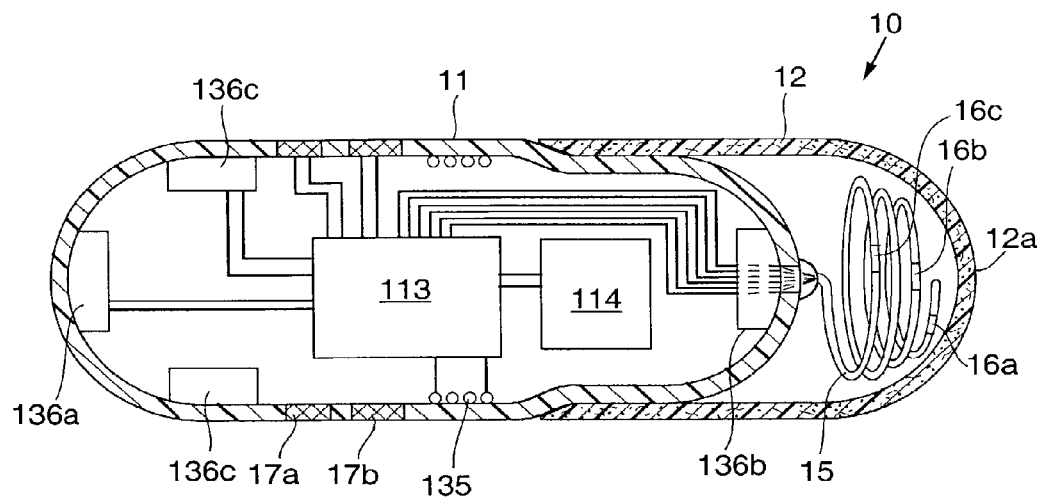

FIG. 15 is a partial cross-sectional view of a fifth embodiment of a capsule of the present invention having a dissolvable encasing containing a deployable stimulation electrode.

Figure 16:
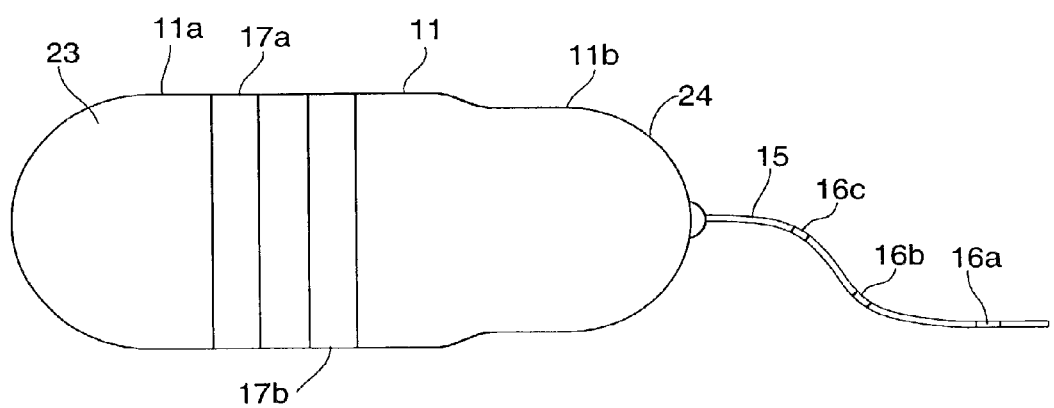

FIG. 16 is a side elevational view of the capsule shown in FIG. 15 with the encasing dissolved and the deployable stimulation electrode deployed.

Figure 17A:
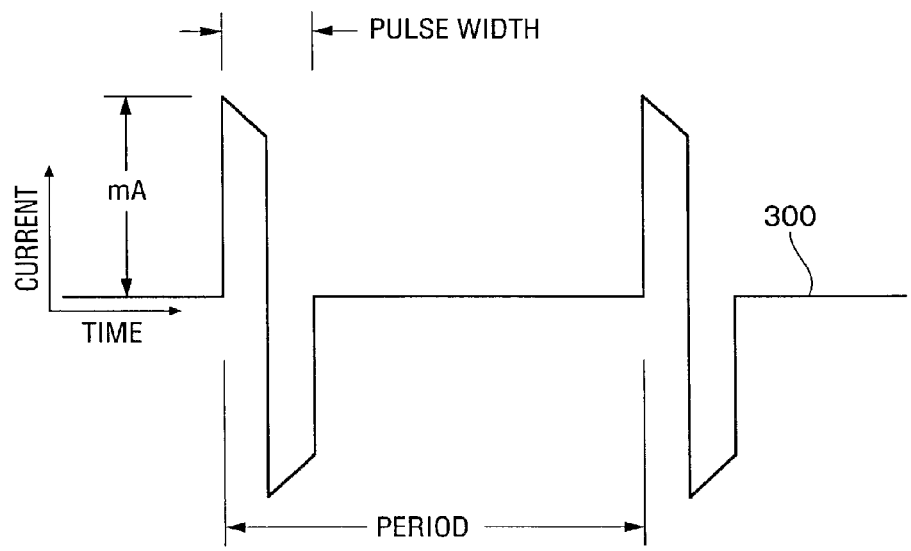
Figure 17B:
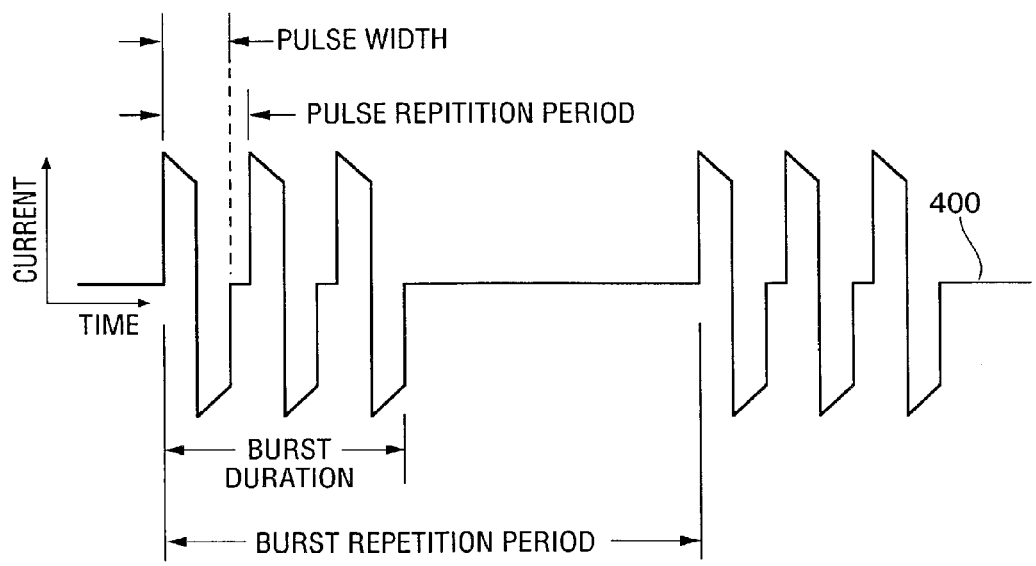

FIGS. 17A and 17B are graphs showing the programmable pacing parameters of the capsule shown in FIGS. 15 and 16.

Figure 18:
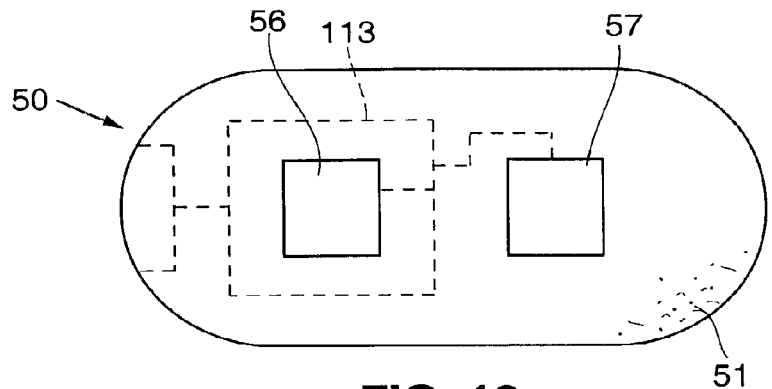

FIG. 18 is a side elevational view of a sixth embodiment of the capsule of the present invention.

Figure 19:
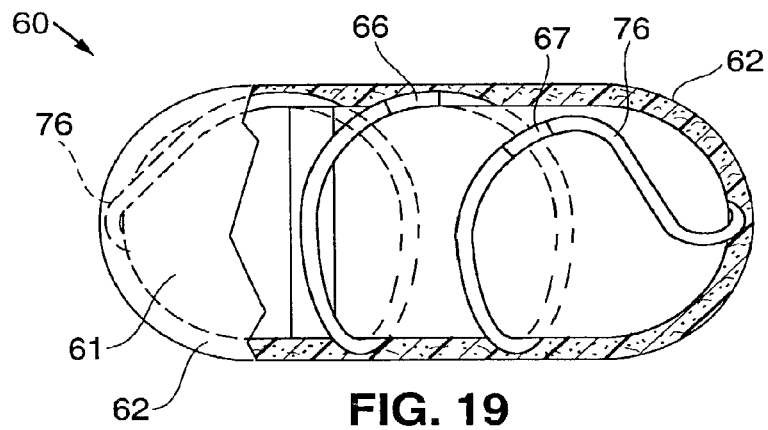

FIG. 19 is a cut away view of a seventh embodiment of a capsule of the present invention and showing stimulation electrodes wrapped about the capsule and encapsulated in a dissolvable encasing that is partially cut away.

Figure 20:
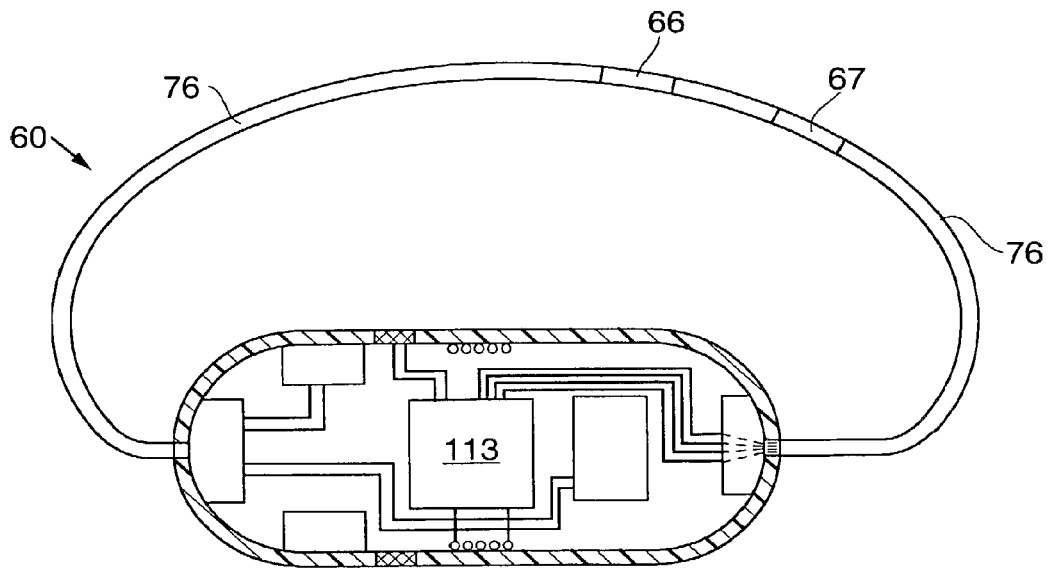

FIG. 20 is a partial cross sectional view of the embodiment of FIG. 19 with the electrodes deployed.

Figure 21:
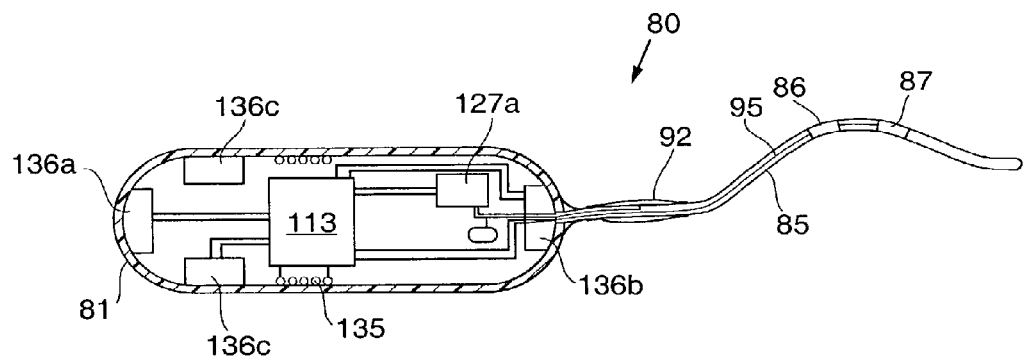

FIG. 21 is a partial cross sectional view of an eighth embodiment of a capsule of the present invention with pressure sensing capabilities.

Figure 22:
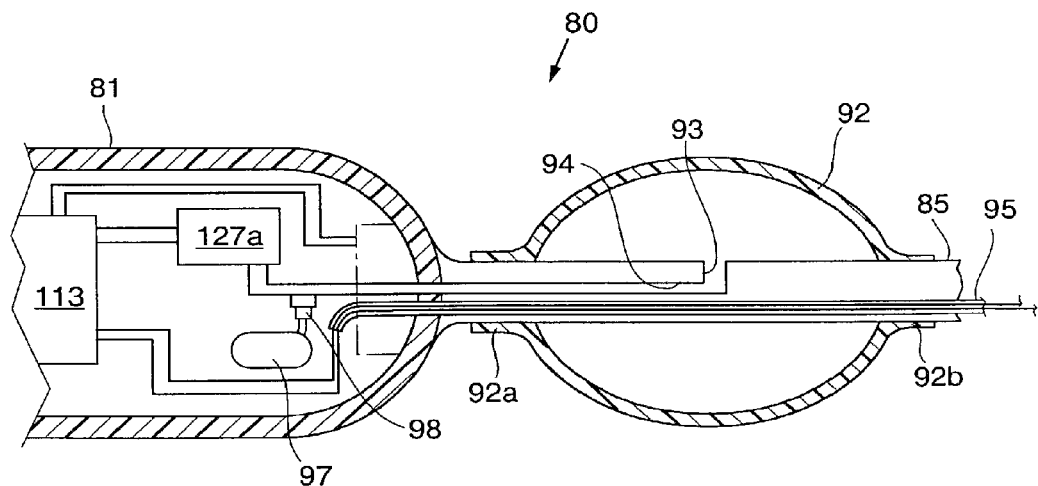

FIG. 22 is an enlarged cross sectional view of a portion of the capsule shown in FIG. 21.

Figure 23:
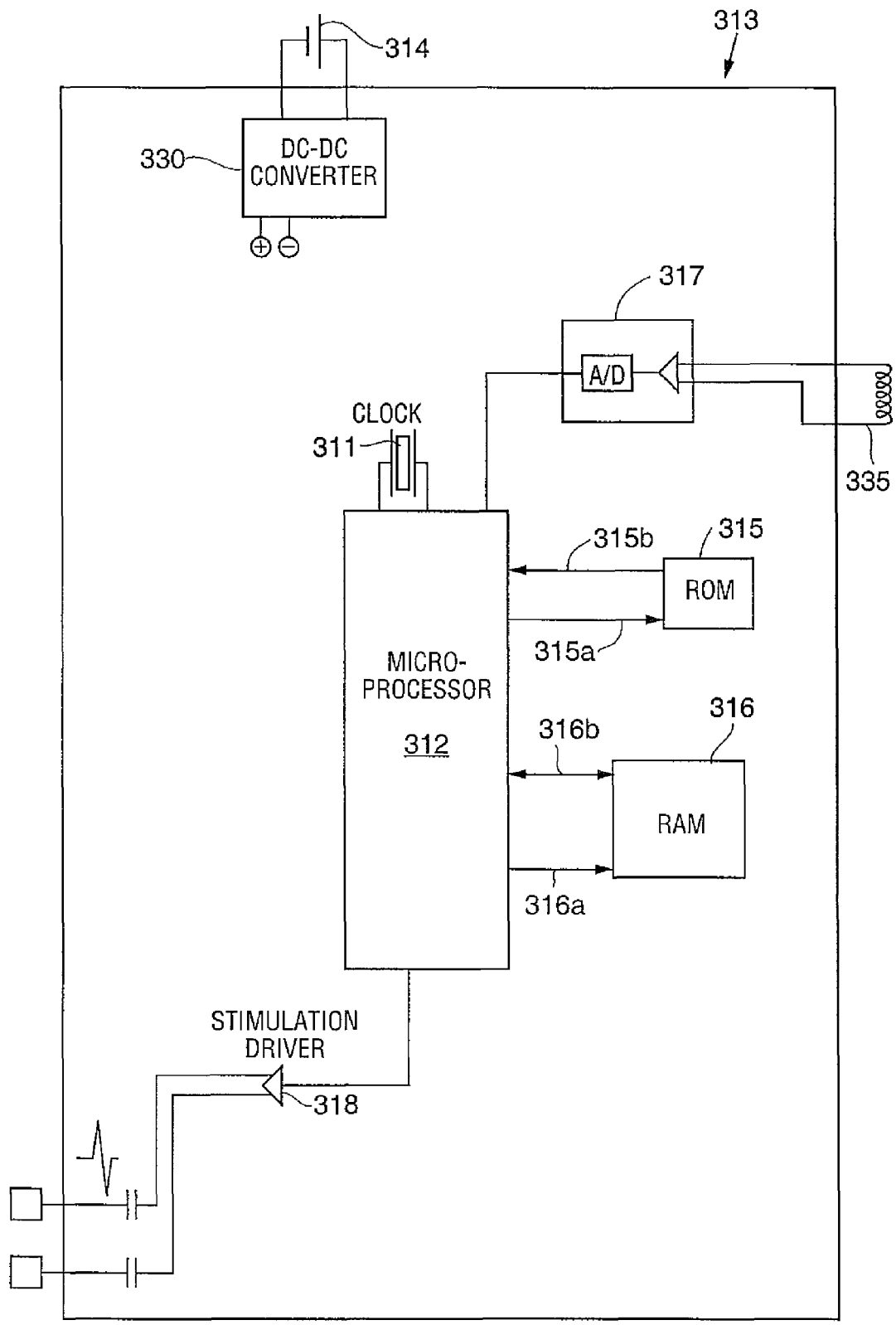

FIG. 23 illustrates alternative electronic circuitry that may be used with the stimulation capsule.

DETAILED DESCRIPTION OF THE PREFERRED EMBODIMENTS

Figure 1:
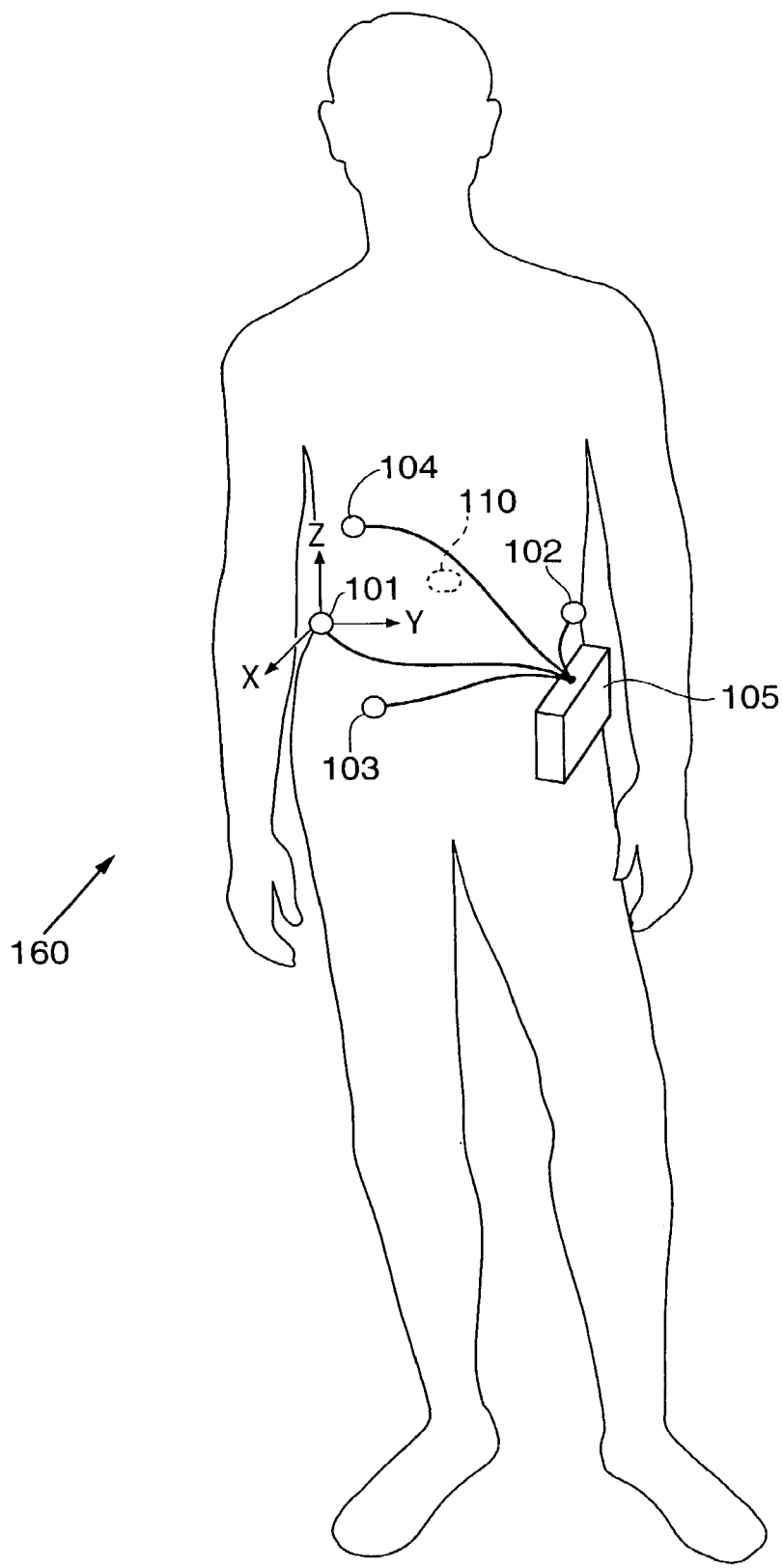
FIG. 1 illustrates the tracking system of the present invention positioned on a user.

Referring to FIG. 1, there is illustrated a tracking system 160 of the present invention positioned on a patient. The tracking system 160 comprises an external recorder 105; four pods 101, 102, 103 and 104 respectively, containing both acoustic and EM emitter/receivers; and a capsule 110 that is swallowable or otherwise positionable to move within an intestinal tract. The recorder 105 is secured to the external abdomen of the patient. The pods 101, 102, 103 and 104 are adhered to the skin of the patient and have an acoustic transmitting/coupling material, e.g., a gel layer, interfacing between the skin of the patient and the pods 101, 102, 103, 104.

Figure 2:
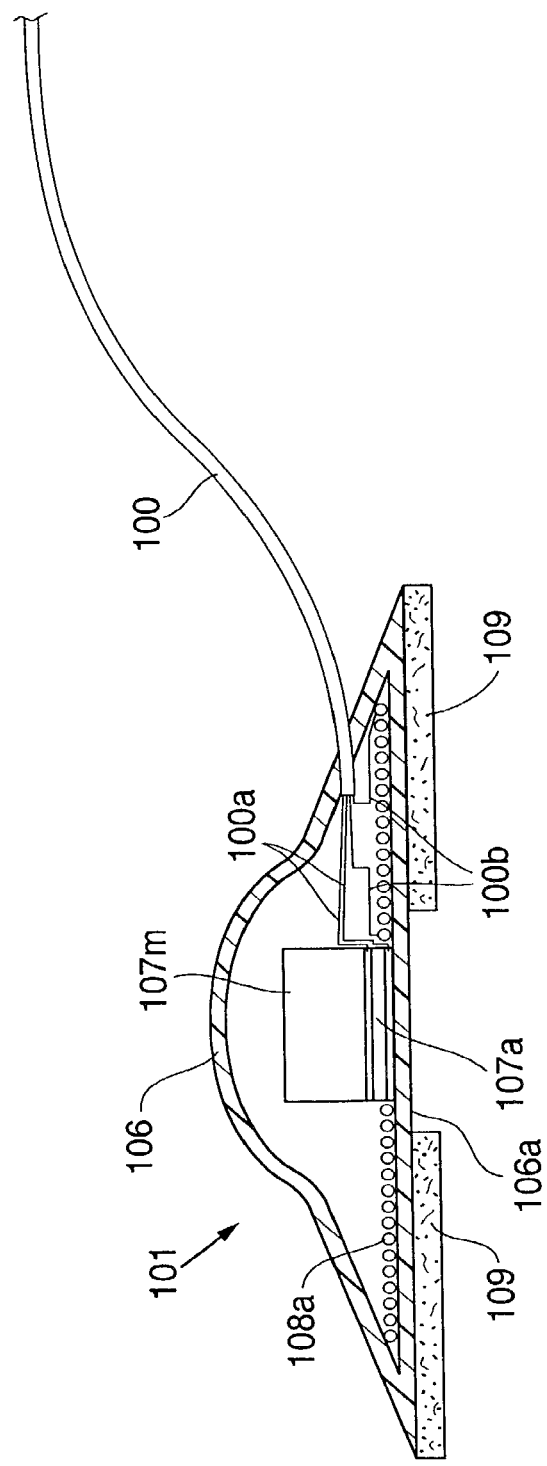
FIG. 2 is a side partial cross-sectional view of a pod of the tracking system of FIG. 1.

As illustrated in FIG. 2, the pod 101 comprises an outer plastic casing 106 enclosing an acoustic transducer 107a and an RF coil 108a. The casing 106 has an interfacing wall 106a for interfacing with the skin of a patient. An adhesive layer 109 is formed on a portion of the interfacing wall 106a, for adhering the pod 101 to the patient's skin while a remaining portion of the interfacing wall 106a is exposed to the patient's skin. The acoustic transducer 107a is attached to the wall 106a within the casing 106 adjacent the exposed portion of the wall 106a in a manner that allows the acoustic or ultrasonic energy to transmit through the interfacing wall 106a. On the opposite side of the acoustic transducer 107a, an acoustic backing material 107m is provided that absorbs the acoustic energy transmitted in the direction towards the backing material 107m. Typically a gel or other acoustically transmitting/coupling material is placed on the outside of the exposed portion of the interfacing wall 106a. The output of the acoustic transducer 107a is coupled to wires 100a that are coupled to the recorder 105 through the wire conduit 100 extending out of the casing 106. The RF coil 108a is coupled through wires 100b also extending through wire conduit 100 to recorder 105. Pods 102, 103, and 104 are similarly constructed.

Figure 3A:
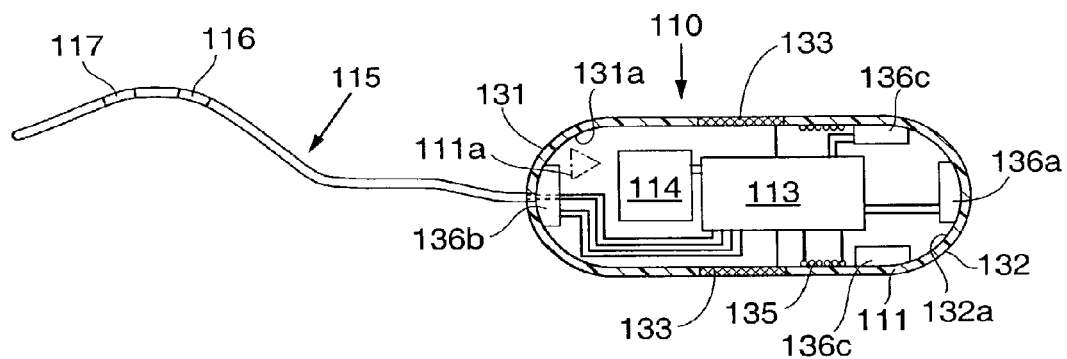
FIGS. 3A and 3B are partial cross-sectional views of a first embodiment of a capsule of the present invention with tracking capabilities, used with the tracking system of the present invention.
Figure 3B:
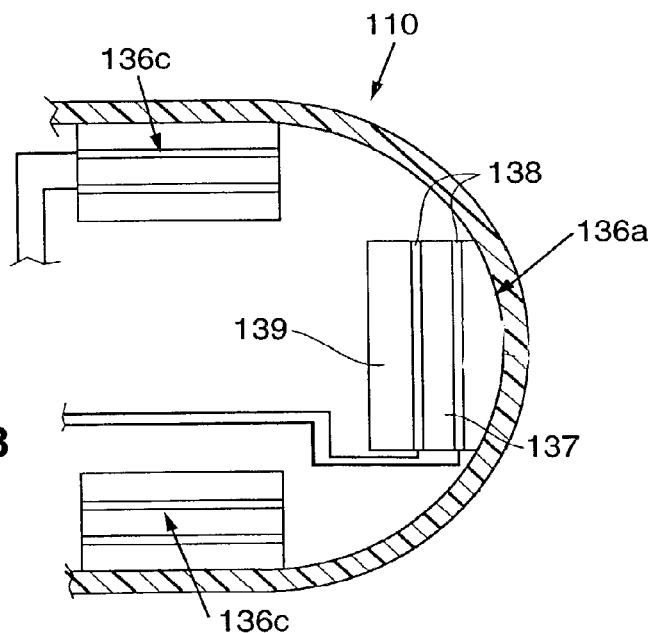

As illustrated in FIGS. 3A and 3B, a first embodiment of a capsule 110 comprises a liquid impermeable and airtight capsule body 111. In general, the capsule of the present invention is sized so that it is capable of being ingested for passage through the intestinal tract. For adult human use, a preferred embodiment of the capsule is to be sized so that it has a length ranging from about 1.5 to 2.5 cm and having a diameter of about 8 mm or less. For children and larger and smaller animals, the capsule can be appropriately sized. The capsule body 111 contains and protects the enclosed circuitry from body fluids while passing through the intestinal tract. At least a portion of the capsule body 111 is constructed of an ultrasound transmitting material that is compatible for use in the human body such as, for example, a medical grade plastic, e.g., polyethylene. A radiopaque marker 111a is embedded in the plastic casing so that in the event it is necessary to locate the device via an external imaging source, its location may be identified. A dissolvable encasing (not shown) may surround the capsule body 111. The encasing may be formed of a suitable dissolvable material such as, for example, a soluble gelatin or enteric coating that is dissolvable in the body fluids contained in the stomach or intestinal tract. Such materials may be selectively dissolved based on the pH condition so that the encasing dissolves after the capsule 110 has passed through the highly acidic stomach and into the more neutral small intestine. The capsule body 111 includes a generally hemispherical back end 131 and a generally hemispherical front end 132. The back end 131 includes an inner end surface 131a. The front end 132 includes an inner end surface 132a. The overall conformation of the ingestible capsule 110 is cylindrical in shape forming a substantially smooth outer capsule surface.

The capsule 110 includes an RF coil 135 for transmitting and receiving RF signals, and an acoustic transducers 136a, 136b, and 136c located within the capsule body 111. The acoustic transducers 136a and 136b are located against the inner end surfaces 132a and 131a respectively with an acoustic transmitting/coupling material filling any gap between the transducers 136a and 136b and the end surfaces 132a, 131a in a manner so that the transducers can transmit acoustic, preferably ultrasonic waves through the capsule body 111 to the surrounding tissue or material. Acoustic transducer 136c is cylindrical in shape, extending around an inner circumference of the capsule. An acoustic transmitting/coupling material similarly fills any gap between the acoustic transducer 136c and the inner wall of the capsule body 111. The acoustic transducers 136a-c are arranged in combination to transmit acoustic signals relatively omni-directionally.

The transducer 136a comprises a piezoelectric crystal 137 located between electrode plates 138 that when energized cause the crystal to oscillate at an ultrasonic frequency (preferably between 100 kHz and 5 MHz). An acoustic backing material 139, such as, oxide particles in a flexible polymer, e.g., an epoxy matrix tungsten powder, is placed on the back of the transducer 136a to absorb any acoustic transmissions in a direction opposite to the end surface 132a. The acoustic transducers 136b and 136c are constructed in a similar manner to transducer 136a and of similar materials. Other configurations of an acoustic transducer or transducers may be used to provide relatively omni directional acoustic signal transmission. The RF coil 135 and the acoustic transducers 136a, 136b and 136c are electrically coupled to the electronics 113 which is powered by battery 114.

An elongate member 115 is affixed to the back end 131 of the capsule body 111. First and second bipolar electrodes 116, 117 are located on the elongate member 115, the second bipolar electrode 117 being electrically opposite of the first electrode 116. The elongate member 115 is preferably formed of an elastically behaving material such as a Ni—Ti alloy.

The capsule body 111 also includes a pH sensor 133 on the capsule body 111. The pH sensor 133 is formed with dissimilar metals such as, e.g., silver chloride and antimony that sense differences in pH and convert the sensed result into a calibrated electrical signal. The pH sensor is coupled to the electronics 113 by electrical conductors.

Figure 4:
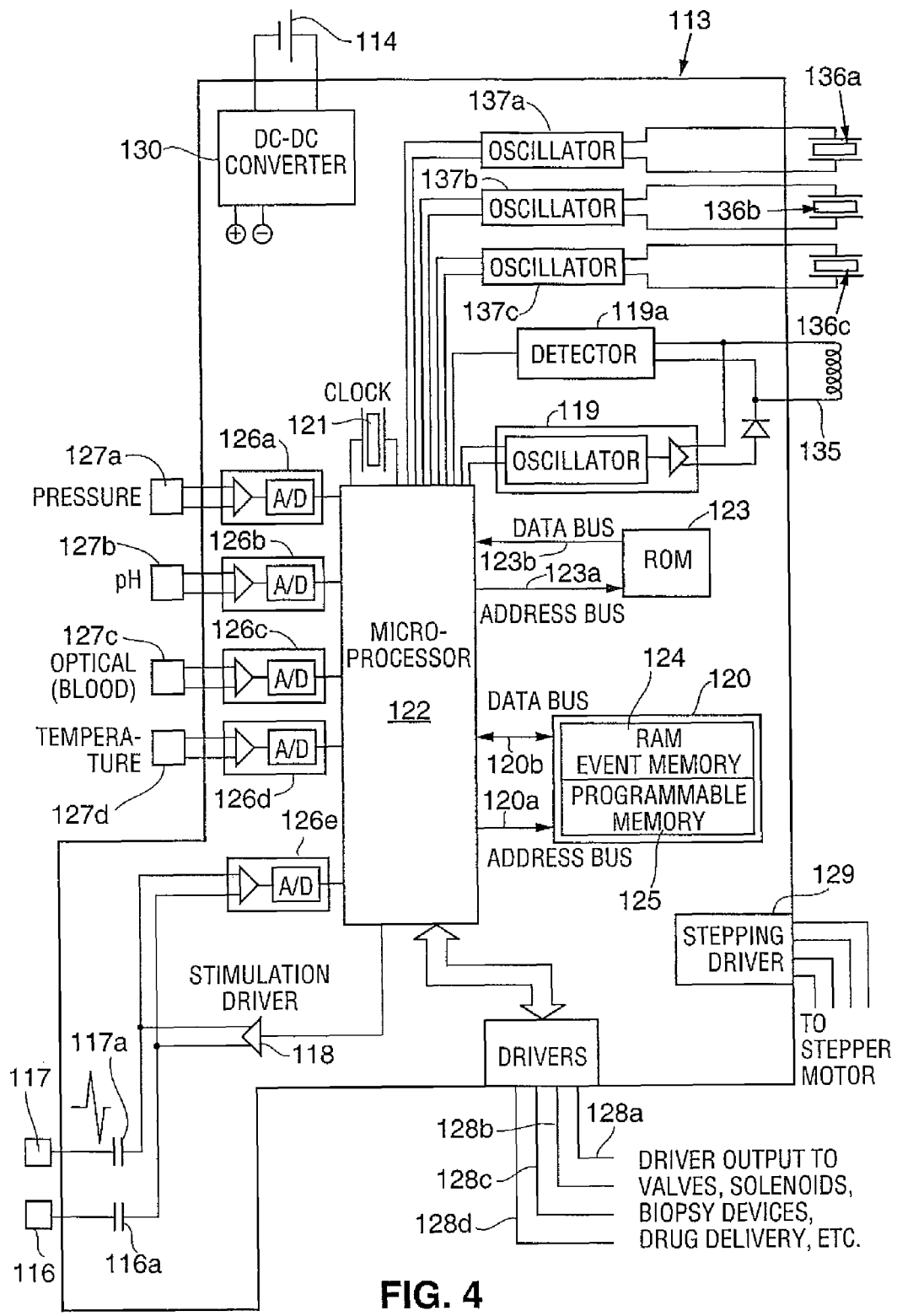
FIG. 4 illustrates the electronic circuitry of the capsule illustrated in FIG. 1.

Referring now to FIG. 4, the electronic circuitry 113 of the capsule 110 is illustrated. The electronic circuitry 113 is a chip that includes a number of optional connectors, and, as such, may be used in a number of different diagnostic or therapeutic capsule configurations. The electronic circuitry 113 of the capsule 110 comprises, a microprocessor or controller 122 for controlling the operations of the electronic circuitry, an internal clock 121, and battery device 114 such as a pair of lithium iodine batteries, for powering the various components of the circuit 113. As such, the controller 122 and battery device 114 are coupled to each of the major components of the circuit as would be known to one of ordinary skill in the art.

The controller 122 is coupled to ROM 123, which contains the program instructions for the controller 122 and any other permanently stored information that allows the microprocessor/controller 122 to operate. The controller 122 addresses memory in a location in ROM 123 through address bus 123a and the ROM 123 provides the stored program instruction to the controller 122 via data bus 123b.

The electrode plates 138 of the acoustic transducer 136a are powered through oscillator 137a controlled by the controller 122 to produce a desired acoustic wave output. Similarly, electrode plates of acoustic transducers 136b and 136c are powered through oscillators 137b and 137c, respectively, controlled by the controller 122. The controller 122 controls the RF coil 135 that acts either to deliver an RF tracking signal or as a telemetry device for communicating data to the recorder 105. The RF coil 135 delivers signals to or receives signals from the RF coils 108a-d (FIG. 5) in the pods 101, 102, 103, and 104. For tracking purposes, controller 122 will respectively, at fixed time intervals, order the transmission of an RF signal and an acoustic signal using the RF coil 135 and at least one of acoustic transducers 136a-136c. The controller's commands will incorporate a preset time interval between the RF signal transmission and acoustic signal initiation. Such time interval (which could be zero) will be factored in at the recorder 105 to determine acoustic wave transmission time. In the preferred embodiment, the capsule's acoustic transducers 136a-136c transmit the acoustic signals immediately, or a defined time after the RF reference signal. The acoustic transducer 136a will emit a first signal a predetermined time after the RF signal, the second and third acoustic transducers 136b and 136c will emit second and third signals respectively at predetermined times after the RF signal and sufficiently spaced in time from the other signals so that the acoustic signals may be differentiated. Alternatively, the second and third acoustic signal may be referenced from second and third differentiated RF signals.

When the RF coil 135 is receiving an external telemetry signal, the buffered oscillator 119 is disabled. Telemetry signals received on RF coil 135 are detected in a detector circuit 119a and communicated to microprocessor 122. The detector circuit 119a is preferably selected based on the modulation used for the telemetry signals.

One or more sensors, e.g., 127a (pressure), 127b (pH), 127c (optical), 127d (temperature), and 116, 117(electrodes) may be coupled to controller 122 through A/D converters (with amplifiers) 126a, 126b, 126c, 126d, 126e which convert a representative analog electrical signal into a digital signal. Suitable sensors of these types are generally known in the art and may be located within, on, or external to the capsule body 111. The electrodes 116, 117 used to deliver the stimulation are also used to sense electrical activity or impedance as described in further detail herein.

The controller 122 is coupled to RAM 120 via an address bus 120a for addressing a location in RAM 120 and a bi-directional data bus 120b for delivering information to and from RAM 120. The RAM 120 includes event memory 124 that temporarily stores data recorded by sensors 127a-127d and electrodes 116, 117. RAM 120 also includes a programmable memory 125 which may be programmed, for example, via telemetry while the capsule 110 is within the intestinal tract, to provide treatment protocols. The data stored in the event memory 124 may be sent to external coils 108a-d (FIG. 5) intermittently as data bursts via telemetry through the RF coil 135, as opposed to continuously in order to save battery power. The data stored in the programmable memory 125 may include specifications for the electrical stimulation operating modes (e.g. waveform, type of stimulation: for pacing, inducing contraction or other type) and various procedure parameters (e.g., when to deliver a drug or electrical stimulation). Such programming may be done in response to sensed information or it may be done automatically by an external controller or as desired by a treating physician, etc.

Controller 122 is coupled to a buffered oscillator 119 that provides an RF signal to be emitted from the RF coil 135. The RF signal is preferably at about 100 kHz to about 5 MHz so that the signal is efficiently transmitted through tissue. The controller 122 controls the oscillator 119 and provides data for example, various sensed data such as pressure, pH, impedance, electrical activity, etc., to be modulated with the RF signal to be delivered through RF coil 135. The controller 122 may also be coupled through stimulation driver 118 and coupling capacitors 116a, 117a to bipolar stimulating electrodes 116, 117, respectively. Electrical stimulation may be provided in a manner similar to that described herein with reference to the stimulating electrodes 16a-c, 17a-b, 56, 57, 66, 67, 86, and 87 of FIGS. 15-22. The stimulation modes and parameters can be preprogrammed or set by an external device that telemetrically communicates the parameters.

The battery 114 has its output supplied to a DC-to-DC converter 130 to provide a higher voltage, which is utilized for electrical stimulation pulses. The DC-to-DC converter 130 is conventional and provides an output voltage of 15 to 20 volts. Further the circuit 113 may include one or more drivers 128a, 128b, 128c, 128d that drive various devices, for example, diagnostic or therapeutic electromechanical devices, such as controlling valves, solenoids, etc, for, e.g., drug delivery, biopsy, content sampling, or a marker release, etc. The controller 122 provides a signal to a driver 128a-128d based on a preset program in ROM 123, on sensed parameters stored in RAM 120, and/or on a telemetrically received signal from the recorder 105 or RF coils 108a-d in the pods, 101-104. The circuit may also include a stepping driver 129 coupled to a stepper motor for example for rotating an imaging device (e.g., diagnostic ultrasonic device) or actuating a biopsy device, etc.

Figure 5:
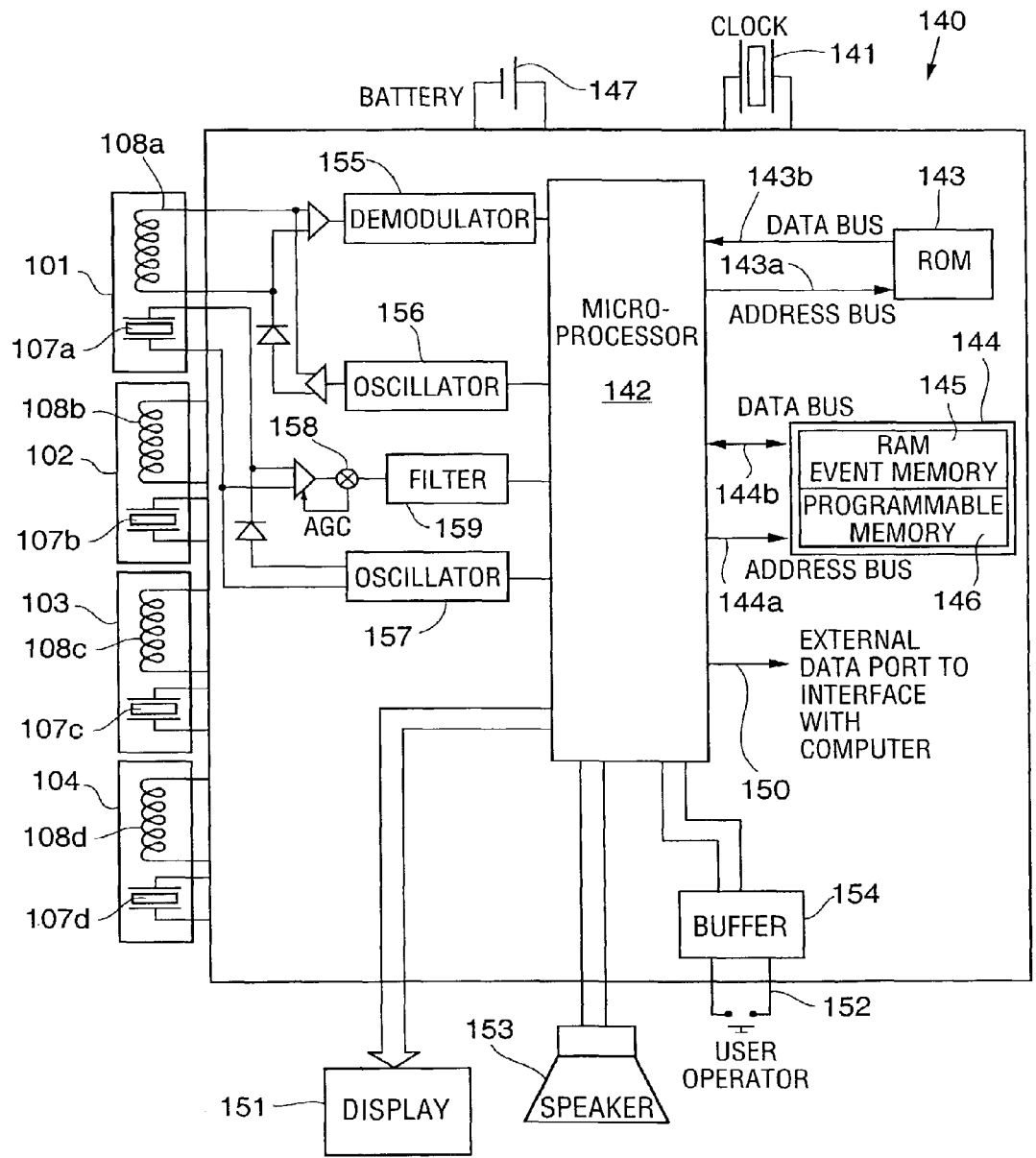
FIG. 5 illustrates a schematic of the electronics of the recorder of the tracking system of the present invention.

Referring now to FIG. 5, a schematic of the electronic circuitry 140 of the recorder 105 of the present invention is illustrated. The electronic circuitry 140 of the recorder 105 comprises: a microprocessor or controller 142 for controlling the operations of the electronic circuitry, an internal clock 141, and power source such as a battery 147 for powering the various components of the circuit 140. The controller 142 and battery device 147 are coupled to each of the major components of the circuit in a manner known to one of ordinary skill in the art.

The electronic circuitry 140 is coupled to the pods 101, 102, 103 and 104, which respectively include RF coil sensors 108a-d and acoustic transducers 107a-d that send and receive signals to and from the capsule 110. The details of the coupling of the transducer 107a and 108a are illustrated in FIG. 5. The transducers 107b-d and coils 108b-d are coupled in a similar manner not shown. The output of the RF coil 108a is coupled through a demodulator 155 to the controller 142. The demodulator 155 demodulates the information carried by the RF signal received by the RF coil 108a. Such information may include, for example, telemetrically delivered sensed data. Also, the RF coil 108a may emit an RF reference signal. The controller 142 controls the output of the RF coil 108a, which communicates with the capsule 110. The controller 142 is coupled to an oscillator 156 that provides a carrier signal, preferably having a characteristic frequency in the range of 100 kHz to 5 MHz so that it may be efficiently transmitted through tissue to the capsule. The controller 142 provides data to be modulated with the RF signal, for example, commands to the capsule 110 to provide treatment, treatment parameters, etc. The controller 142 controls the output of acoustic transducer 107a through oscillator 157, which provides the oscillating frequency to the transducer when the pod is pinging another pod, i.e., when the pods are sending signals to calibrate the pods and identify their locations on the coordinate system. The controller 142 also receives the representative acoustic signal from the transducer 107a through automatic gain control device 158 which brings the voltage or current levels within a predefined range, and through filter 159.

The controller 142 is further coupled to ROM 143, which contains the program instructions for the controller 142 and any other permanently stored information that allows the microprocessor/controller 142 to operate. The controller 142 addresses memory in ROM 143 via address bus 143a and the ROM 143 provides the stored program instruction to the controller 142 via data bus 143b.

The controller 142 is coupled to RAM 144 via address bus 144a and bi-directional data bus 144b. The RAM 144 comprises event memory 145 that temporarily stores data sent via telemetry from the capsule 110 to the RF coils 108a-d in the pods 101-104 until the data is downloaded onto a computer using external data port 150. For tracking purposes, the RAM 144 is also used to store the data concerning lag times between the RF signal and acoustic signals received by transducers 107a-d, and RF coils 108a-d in the pods 101-104. The RAM 144 also comprises a programmable memory 146, which is used to specify operation modes (e.g. waveform, type of stimulation: for pacing, inducing contraction or other type) and various procedure parameters that may be transmitted to the capsule 110 through RF coils 108a-d via telemetry. The recorder 105 also includes a display 151 to show recorded data, sensed parameters, treatment parameters, and status of device (e.g., capsule position, battery charge status, etc.). The recorder 105 also includes a data input device 152 such as a keyboard, pad or input screen for inputting new parameters, programming the capsule, changing the treatment scheme, viewing various data or turning the device on or off. The input is coupled through a buffer 154 to the controller 142. The controller 142 is coupled to a speaker 153 for providing audible information such as an alert.

Figure 6:
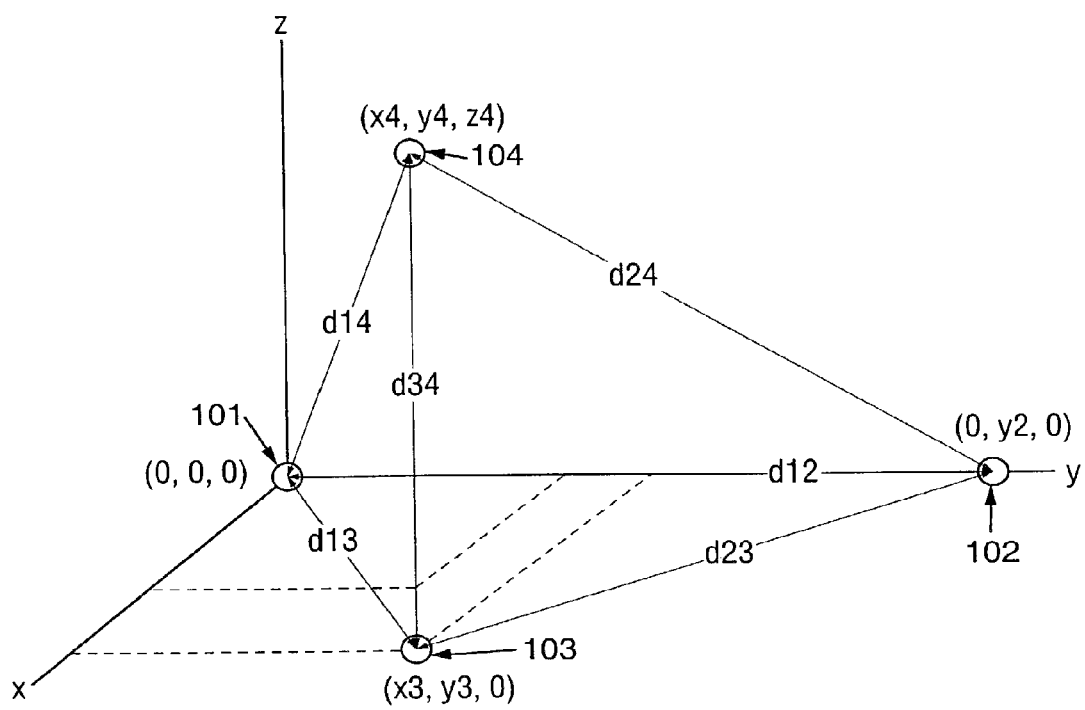
FIG. 6 illustrates the pods such as the one illustrated in FIG. 2 set up in an x, y, z Cartesian coordinate system.
Figure 7:
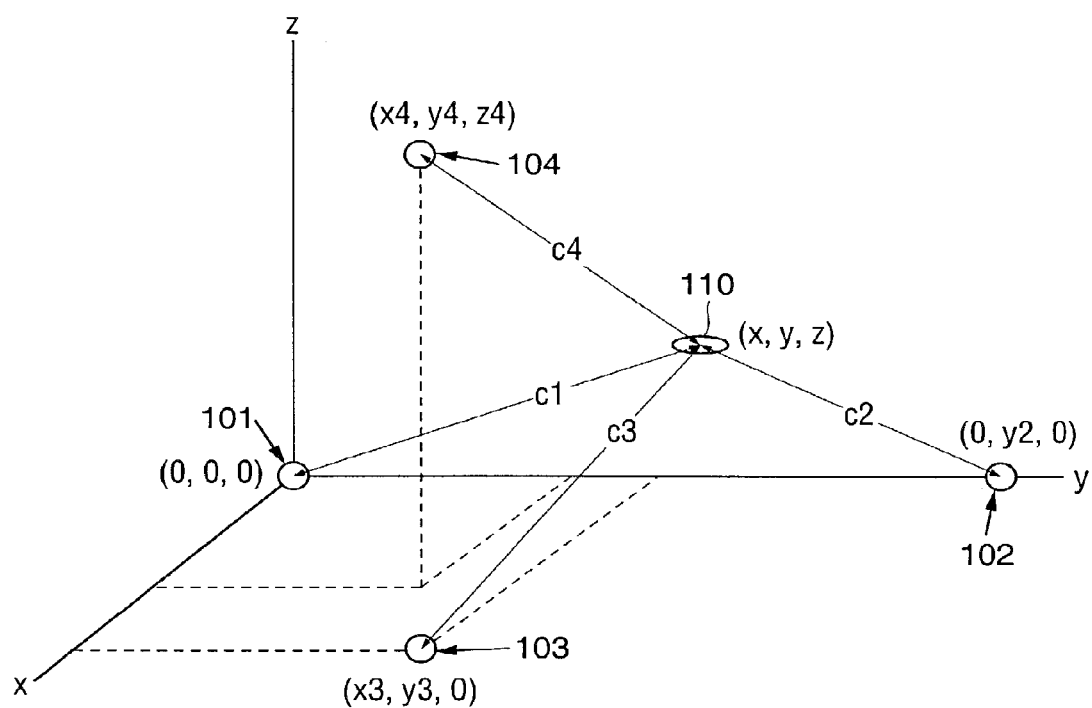
FIG. 7 illustrates the location of a capsule on the x, y, z Cartesian coordinate system of FIG. 6.

In FIGS. 6 and 7, the pods 101, 102, 103, and 104 are set up in an Cartesian (x,y,z) coordinate system. The origin of the coordinate system is defined as the location of pod 101. The y-axis is defined as the line that passes through pod 101 and pod 102. The x-y plane is defined as the plane that intersects pods 101, 102 and 103. The z-axis is perpendicular to the x-y plane. Pod 104 is located off of the x-y plane. Thus, the coordinates of the pods in this defined coordinate system are:

Pod 101: (0, 0, 0)
Pod 102: (0, $y_2$, 0)
Pod 103: ($x_3$, $y_3$, 0)
Pod 104: ($x_4$, $y_4$, $z_4$)

where the pod coordinates $y_2$, $x_3$, $y_3$, $x_4$, $y_4$, and $z_4$ are initially unknown.

Once the pods are placed as illustrated in FIG. 1, the coordinates of the pods are initially determined in the following manner. As illustrated in FIG. 6, the distances $d_{12}$, $d_{13}$, $d_{14}$, $d_{23}$, $d_{24}$, and $d_{34}$ represent the distances between pods 101 and 102, 101 and 103, 101 and 104, 102 and 103, 102 and 104, and 103 and 104, respectively. The pods, which can both emit and receive electromagnetic and acoustic (including ultrasound) signals, will sense time-lags between the RF and acoustic signals sent between the pods along the distances $d_{12}$, $d_{13}$, $d_{14}$, $d_{23}$, $d_{24}$, and $d_{34}$, i.e., the pods will ping each other. The pods communicate with a processor located in the recorder that calculates the distance and determines the coordinates. The time-lags are multiplied by the velocity of sound to calculate the distances ($d_{12}$, $d_{13}$, $d_{14}$, $d_{23}$, $d_{24}$, and $d_{34}$) between the pods.

Under Pythagoras' Theorem the following six equations relate the coordinates of the pods and the distances between them:

$$(x_2-x_1)^2+(y_2-y_1)^2+(z_2-z_1)^2=d_{12}^2 \qquad (1)$$

$$(x_3-x_1)^2+(y_3-y_1)^2+(z_3-z_1)^2=d_{13}^2 \qquad (2)$$

$$(x_4-x_1)^2+(y_4-y_1)^2+(z_4-z_1)^2=d_{14}^2 \qquad (3)$$

$$(x_3-x_1)^2+(y_3-y_1)^2+(z_3-z_1)^2=d_{23}^2 \qquad (4)$$

$$(x_4-x_1)^2+(y_4-y_1)^2+(z_4-z_1)^2=d_{24}^2 \qquad (5)$$

$$(x_4-x_1)^2+(y_4-y_1)^2+(z_4-z_1)^2=d_{34}^2 \qquad (6)$$

The pod coordinates $x_1$, $y_1$, $z_1$, $x_2$, $z_2$, and $z_3$ are defined as having the value of 0. Thus, plugging in the known pod coordinates, the equations can be rewritten as:

$$y_2^2=d_{12}^2 \qquad (1')$$

$$x_3^2+y_3^2=d_{12}^2 \qquad (2')$$

$$x_4^2+y_4^2+z_4^2=d_{14}^2 \qquad (3')$$

$$x_3^2+(y_3-y_2)^2=d_{23}^2 \qquad (4')$$

$$x_4^2+(y_4-y_2)^2+z_4^2=d_{24}^2 \qquad (5')$$

$$(x_4-x_3)^2+(y_4-y_3)^2+z_4^2=d_{34}^2 \qquad (6')$$

With these six equations, and the determined distances, $d_{12}$, $d_{13}$, $d_{14}$, $d_{23}$, $d_{24}$, and $d_{34}$, the six pod coordinates, $y_2$, $x_3$, $y_3$, $x_4$, $y_4$, and $z_4$ may be solved. Single solutions for all the coordinates may be obtained by setting the following position restrictions: $y_2>0$; $x_3>0$; and $z_4>0$. In other words, pod 101 should be placed on the right side of the user, pod 102 on the left side, pod 103 on the lower abdomen, and pod 104 on the upper abdomen as illustrated in FIG. 1.

The determination of the solutions for the six pod coordinates $y_2$, $x_3$, $y_3$, $x_4$, $y_4$, and $z_4$ are described below:

Equation (1') gives:

$$y_2 = d_{12} \tag{1''}$$

Plugging (1'') into (4') and subtracting (4') from (2') gives:

$$y_3 = (d_{12}^2 + d_{13}^2 - d_{23}^2)/(2d_{12}) \tag{2''}$$

Plugging (2'') back into (2') gives:

$$x_3 = (d_{13}^2 - y_3^2)^{0.5} \tag{3''}$$

where $y_3$ has been solved above.

Plugging (1') into (5') and then subtracting (5') from (3') gives:

$$y_4 = (d_{12}^2 + d_{14}^2 - d_{24}^2)/(2d_{12}) \tag{4''}$$

Subtracting (6') from (3') gives:

$$x_4 = (d_{14}^2 - d_{34}^2 + x_3^2 + y_3^2 - 2y_3 y_4)/(2x_3) \tag{5''}$$

where $x_3$, $y_3$ and $y_4$ have been solved above.

Plugging (4'') and (5'') into (3') gives:

$$z_4 = (d_{14}^2 - x_4^2 - y_4^2)^{0.5} \tag{6''}$$

where $x_4$ and $y_4$ have been solved above.

The pod coordinates are determined whenever the pods are repositioned. The pod coordinates may also be re-established at regular intervals to account for movement and thus relative change in pod position.

As illustrated in FIGS. 7 and 8A-G, using the coordinates of the pods, the location of the capsule in space may be determined as follows. The range-finding capability of the pods measure the distances between the capsule 110 and each pod. As illustrated in FIGS. 8A-B, the capsule 110 emits an RF signal 205 and a synchronized ultrasonic signal 206 that is emitted a predetermined time interval after the RF signal 205 is emitted. In the preferred embodiment the ultrasound signal 206 is emitted immediately following the RF signal 205. In this drawing, for illustrative purposes the signal emitted from transducer 136a is illustrated. Second and third acoustic signals emitted from the second and third transducers 136b and 136c would be similar to the signal emitted from transducer 136a except that they preferably emitted after the first signal 206 and at predetermined time intervals from the RF signal 205. The signals from the additional acoustic transducers 136b and 136c may also alternatively have different waveforms as that of the first signal 206. FIG. 8C illustrates the timing of when the RF signal 205 is received at the pods. FIGS. 8D-G illustrate the timing of when the ultrasound signal 206 is respectively received at pods 101, 102, 103, and 104. Because the RF signal 205 travels at the speed of light, it is received by the pods 101, 102, 103 and 104 at a relatively negligible time delay in comparison to the ultrasonic signal which travels generally at about 1540 meters per second in human tissue. The distances c.sub.1, c.sub.2, c.sub.3, and c.sub.4 represent the distances between the capsule and pods 101, 102, 103, and 104, respectively. The pods 101, 102, 103 and 104 receive the ultrasound signal 206 transmitted from the capsule 110 at varying times depending on the distances c.sub.1, c.sub.2, c.sub.3, and c.sub.4 respectively. Such time lags may be represented as illustrated, for example, in FIG. 8 as t.sub.1, t.sub.2, t.sub.3, and t.sub.4 corresponding to distances c.sub.1, c.sub.2, c.sub.3, and c.sub.4, respectively. The time-lags will then be multiplied by the velocity of sound to calculate the distances (c.sub.1, c.sub.2, c.sub.3, and c.sub.4) between the capsule 110 and each pod.

Using Pythagoras' Theorem the following equations relate the coordinates of the capsule $(x_n, y_n, z_n)$ and pods, and the distance between them:

$$(x_n - x_1)^2 + (y_n - y_1)^2 + (z_n - z_1)^2 = c_1^2 \tag{7}$$

$$(x_n - x_2)^2 + (y_n - y_2)^2 + (z_n - z_2)^2 = c_2^2 \tag{8}$$

$$(x_n - x_3)^2 + (y_n - y_3)^2 + (z_n - z_3)^2 = c_3^2 \tag{9}$$

$$(x_n - x_4)^2 + (y_n - y_4)^2 + (z_n - z_4)^2 = c_4^2 \tag{10}$$

These four equations may be solved to obtain a single solution for the three coordinates of the capsule, $x_n$, $y_n$, and $z_n$.

According to one embodiment, a three-dimensional or four-dimensional map of the capsule's trip through the intestinal system can be generated by measuring the capsule's coordinates at fixed time intervals.

Alternatively, linear travel distance measurements can be made by using Pythagoras' Theorem. Incremental linear distances can be calculated and then summed to obtain a total linear travel distance (L):

$$L = \Sigma_o^m [(x_{n+1} - x_n)^2 + (y_{n+1} - y_n)^2 + (z_{n+1} - z_n)^2]^{1/2},$$

where m is equal to the number of incremental distances and where $(x_n, y_n, z_n)$ and $(x_{n+1}, y_{n+1}, z_{n+1})$ are consecutive capsule coordinate measurements used to measure incremental linear distances traveled. In this manner a linear map of the capsule's position along the intestinal tract may be obtained. Such a map shows the position of the capsule along the tract independent of actual 3D spatial orientation. Thus, errors based on intestinal shifting, peristaltic motion, patient positioning, and change in pod location are reduced without requiring additional sensed information. Retrograde peristaltic motion can occur in the small intestine. An algorithm may be used to cancel out any backtracking travel measurements when calculating the linear distance traveled by the capsule. As described below using an additional acoustic transducer, (e.g., located on the opposite end of the capsule) and obtaining the same positional information may provide information on capsule orientation and direction of capsule movement. Preferably, the additional transducer will deliver a signal at time intervals between the acoustic signals of the first transducer. The signals from the additional transducer may have a different waveform to differentiate the signal from signals corresponding to the first transducer. The orientation information may provide additional information that is used to cancel out retrograde capsule movement.

Referring to FIGS. 11A-D, an example of a linear map of an intestinal tract and corresponding maps of sensed information are illustrated. FIG. 11A illustrates an example of a linear map of a gastrointestinal tract. FIG. 11B illustrates an example of a map of pH sensed by a capsule in relation to its linear position along the length of the tract of FIG. 11A. FIG. 11C illustrates an example of a map of pressure sensed by a capsule in relation to its linear position along the length of the tract of FIG. 11A. FIG. 11D illustrates an example of a map of electrical activity sensed by a capsule in relation to its linear position along the length of the tract of FIG. 11A. These maps may be plotted from sensed information on a display screen in the illustrated format or as otherwise may be desirable by a user.

The parameters shown in the maps in FIGS. 11B-D may be determined by a capsule having sensing capabilities. As the capsule passes through the intestinal tract and its location along the length is determined, other parameters relating to the condition of the intestinal tract may be sensed periodically or continuously. The sensed conditions may be sent via telemetry to one or more pod receivers. This may occur independently from the time of the RF reference signal transmission and the acoustic signal transmission so that the telemetry signal is independent of the coordinate determining RF reference signal. The sensed information is mapped along the length of the intestine by the tracking system as described above. A linear map of sensed information is overlaid on the linear map of the intestine so that unusual parameter values, or areas to be treated may be determined. Upon a second pass of a capsule, the area or portion of the tract to be treated may be located along the length of the linear map created from the first capsule pass. The second capsule uses a similar method to determine its position along the length of the tract and its linear travel position is compared to the linear travel position of the first capsule. Thus, when the capsule has traveled the appropriate position along the tract, the segment of the tract may then be treated. Treatment may be triggered by a telemetric signal sent to the capsule when the recorder and external controller have calculated the appropriate linear position.

Referring now to FIG. 9, there is illustrated a second embodiment of a treatment capsule of the present invention. Capsule 170 comprises a capsule body 171 including an electronic circuit 113 and battery 174 coupled to the electronic circuit 113. An RF coil 175 and acoustic transducers 176a-c operate in a similar manner as RF coil 135 and transducers 136a-c described herein. The capsule further comprises a compressed gas source 165 and an inflatable balloon 167 externally fixed to the capsule body 171. The gas source 165 is in fluid communication with a valve 166 that opens into a chamber 168 in the balloon 167. The chamber 168 of the balloon 167 further is in fluid communication with a valve 169 that opens to a gas exit port 172 that is in fluid communication with the intestinal tract. The valves are coupled through drivers 128a, 128b in electronic circuit 113. The operation of the valves 166, 169 is controlled by the controller 122 in the electronic circuit 113. In use, the capsule is delivered after a diagnostic capsule using an optical sensor has been passed through the intestinal tract to obtain a map of optically sensed parameters along the length of the tract. After a blockage site along the length has been determined, the capsule 170 is ingested. Using the RF coil 175 and acoustic transducers 176a-c of the tracking system described above, the tracking system identifies when the capsule 170 has reached the blocked site. The tracking system sends a telemetric control signal to the RF coil 175 that instructs the controller 122 to inflate the balloon 167. The controller activates valve 166 through driver 128a which opens to allow compressed gas from the gas source 165 to fill the chamber 168 of the balloon. The inflation of the balloon 167 expands the intestinal wall at the site of the balloon 167 to open the blockage. The controller 122 then opens the valve 169 through driver 128b to allow the gas to escape from the chamber 168 through the gas exit port 172 and into the intestinal tract. The controller may release the gas upon an external telemetrically delivered command that is initiated by, for example, a physician who is observing the capsule and balloon under fluoroscopy, to determine if and when a blockage has been opened. Alternatively, the balloon may be preprogrammed to expand for a predetermined amount of time. The expandable member may be used for a variety of diagnostic or treatment purposes, for example, pressure sensing, opening partial blockages, measuring the openings of partially blocked or constricted areas, providing hemostasis, delivering therapeutic substances that are coated on the balloon 167, or affixing a capsule in an identified location to mark the location in the intestine. An expandable support member such as a stent may be provided on the balloon for placement within a stricture upon expansion of the balloon. Alternatively, the capsule may be provided with a self-expanding support structure such as a self-expanding stent.

FIG. 10 illustrates a third embodiment of a treatment capsule of the present invention. Capsule 180 comprises a capsule body 181 including an electronic circuit 113 and battery 184 coupled to the electronic circuit 113. An RF coil 185 and acoustic transducers 186a-c operate in a similar manner as RF coil 135 and transducer 136a-c described herein. The capsule further comprises a pump 187 filled with a dye such as, e.g., fluorescein or methylene blue to provide a surgeon with identification of a site for surgery. Such marker may include, for example a radiopaque marker that may be located with an active x-ray system during a procedure, a radioactive material that may be interrogated by a passive system, a fluorescing compound that is used to identify the location, or a dye that stains through the wall of the intestine. The compounds may assist a surgeon in a laparoscopic or open procedure where such imaging systems are used during the procedure or where visualization, e.g., of a dye or stain is possible. The pump is coupled to a valve 189 by a conduit 188. The pump 187 and the valve 189 are controlled by the controller 122 in the electronic circuitry 113 through drivers 128c and 128d. In use, the capsule 180 is delivered after a diagnostic capsule having a diagnostic sensor has been passed through the intestinal tract to obtain a map of sensed parameters along the length of the tract. After a site along the length of the tract has been identified for surgical intervention, the capsule 180 is ingested. Using the RF coil 185 and acoustic transducers 186a-c of the tracking system described above, the tracking system identifies when the capsule 180 has reached the identified site. The tracking system sends a telemetric control signal to the RF coil 185 that instructs the controller 122 to activate the pump 187. The controller activates the pump 187 through driver 128c. The controller also activates valve 189 through driver 128d which opens to allow dye from the pump 187 to exit the pump through conduit 188 and valve 189 and be sprayed onto the adjacent intestinal wall. The dye thus marks a location for surgical intervention.

The capsule 180 may also be used to release a gas into the intestinal tract at a given location where e.g. a blockage or other anatomical feature is believed to exist. Using fluoroscopy, the anatomy may be observed. Similarly, using a capsule such as capsule 180, a fluid such as a radiopaque fluid may be released near a constriction or other area to be imaged where pump 187 pumps the fluid into the intestinal tract through a conduit 188 and valve 189.

FIGS. 12-14 illustrate a fourth embodiment of a treatment capsule of the present invention. Capsule 210 comprises a capsule body 211 including an electrocautery ablation circuit 213, an electronic circuit 113, and a battery 214 coupled to the electronic circuit 113. The capsule 210 also comprises an elongate member 225 with a larger area return electrode 227 located thereon. The elongate member 225 and electrodes 226, 227 are constructed in a manner similar to elongate member 15 and electrodes 16a, 16b, and 16c described with respect to FIGS. 15-16 herein. A small area ablation electrode 226 is located on the capsule body 211, preferably in the form of a ring. A thermocouple sensor 127d is located on the capsule body 211 immediately adjacent to the ablation electrode 226 so that the sensor can sense the temperature of tissue that is being treated by the ablation electrode 226 and provide a feedback loop to an external controller 142 that regulates the power delivered to the ablation electrode 226. An RF coil 215 and acoustic transducers 216a-c operate in a similar manner as RF coil 135 and transducers 136a-c described herein. In this embodiment, the RF coil 215 operates at a frequency of about 1 MHz.

As illustrated in FIG. 13, the ablation electronics include, an ablation coil 221, electrodes 226, 227, and an ablation circuit 213 including a capacitor 222. The ablation coil 221 that is tuned to a frequency of about 250 kHz, thus the coils 215 and 221 receive different frequencies, enabling them to distinguish between a telemetry signal and an ablation power signal. An external variable power generator 230 (FIG. 14)

supplies an RF signal at 250 kHz through power transmitter coil 231. The ablation signal received by the ablation coil 221 and parallel capacitor 222 (which together form a tuned circuit to separate the ablation signal from the telemetry signal) is then delivered to electrodes 226, 227. The ablation electrode 226 has a considerably smaller area than the return electrode 227 so that the current density is greater at the ablation electrode 226 where the ablation current is to be focused on the adjacent tissue. The thermocouple sensor 127d provides an electrical signal representative of the temperature of the adjacent tissue, through the A/D converter 126d of the capsule circuit 113. The signal is converted to a digital signal that is provided to the controller 122 of the circuit 113. The signal is telemetrically delivered to the controller 142 of the recorder 105 in a manner as described herein.

As illustrated in FIG. 14, the power is controlled by the controller 142 of the recorder 105 which is coupled to the power generator 230 by way of connector 233. The controller 142 in the recorder electronics 140 will regulate the power output to the ablation electronics based on feedback information as sensed by the thermocouple 127d on the capsule body 211 and delivered via telemetry from the capsule RF coil 215. The regulation of the power is significant in this embodiment as the RF ablation signal strength may vary with distance from the capsule, the type of the tissue being treated, the impedance of the tissue being treated. Thus, the temperature feedback loop is intended to prevent over or under heating of the tissue. In addition, the treatment is initiated by a user by activating a switch 234 coupled to the power generator 230.

In use, the tracking system is used in a manner as described above. A location to be treated along the length of the intestinal tract is first identified by a first capsule passing through the tract. Preferably the capsule will have an optical, chemical or other means for determining a location where bleeding is occurring. This location is identified in a subsequent pass of the ablation capsule 210 and the user turns the ablation power on when the appropriate location is identified to ablate or cauterize the tissue that is bleeding. In a variation of the embodiment, a site where bleeding is present may be treated using a subsequently passed capsule having a balloon tamponade, i.e. an inflatable member that uses compression and/or a thrombogenic substance coated on the inflatable member to help cause hemostasis. A capsule embodiment having an inflatable member is described herein with reference to FIGS. 21 and 22.

FIGS. 15-16 illustrate a fifth embodiment of the capsule of the present invention. The capsule 10 comprises a treatment and sensing device that may be used with the tracking system. The capsule 10 is used to sense electrical parameters of the intestinal wall and/or to treat the intestinal tract by electrically stimulating the intestinal wall. The capsule 10 comprises a liquid impermeable and airtight capsule body 11. The capsule body 11 contains electronic circuitry 113, battery 114, RF coil 135 and acoustic transducers 136a-c as described above with reference to FIGS. 3A and 3B. The capsule body 11 protects the enclosed circuitry from body fluids while passing through the intestinal tract. The capsule body 11 is formed of a material that is compatible for use in the human body, for example, a medical grade plastic or polymer.

An elongate member 15 is affixed to an end of the capsule body 11. Electrodes 16a, 16b and 16c are located on the elongate member 15. Two second, larger area electrodes 17a and 17b extend around the width of the capsule body 11. Electrodes 16a-c may be selected in a number of combinations to form electrode pairs to deliver stimulation to the intestinal wall (or alternatively to sense electrical activity of the intestinal wall). Additionally, one or more of electrodes 17a and/or 17b may be utilized to work with one or more of electrodes 16a-16c where current density will be concentrated at the smaller electrode(s) 16a, 16b, and/or 16c. The capsule electronics may include logic to select which electrodes should deliver stimulation pulses for optimal stimulation. The electronics may similarly control which electrodes may be used to sense electrical activity of the intestinal wall. Alternatively, an external processing unit may determine optimal electrode selection that is communicated to the capsule by a telemetry command signal.

In one preferred embodiment, the capsule 11 may be used for stimulation and subsequent measurement of electrical parameters. This function may be used for diagnostic purposes, for example, to determine if the intestinal wall is properly conducting electrical pulses or if the wall at a particular location is an electrically hypo-active or "dead" area. In a preferred embodiment, the capsule electrodes are electrically configured so that a plurality of adjacent electrode pairs can be used where a first pair stimulates the intestinal wall at a first location and the second pair then detects signals at a second location that are propagated from the original stimulation signal. Accordingly, in a variation of one embodiment, to determine if the intestinal wall is electrically abnormal, e.g., is electrically hypo-active, electrodes 17a and 17b are used to deliver a stimulation signal and an electrode pair formed from at least two of electrodes 16a-c are used to sense resulting signals propagated in an orad direction. In a variation of another embodiment, signal propagation in the aboard direction, i.e., from the back of the capsule to the front assuming the front of the capsule is oriented in a direction away from the mouth is determined using an electrode pair formed from at least two of electrodes 16a-c are used to deliver a stimulation signal and electrodes 17a and 17b sense resulting propagated signals.

As illustrated in FIG. 15, a dissolvable encasing 12 surrounds the elongate member 15, the electrodes 16a-c, and at least a portion of the capsule body 11. When encapsulated by the encasing 12, the elongate member 15 is in a coiled or compressed position.

The encasing 12 is formed of a suitable dissolvable material such as, for example, a soluble gelatin or enteric coating that is dissolvable in the body fluids contained in the intestinal tract. Such materials may be selectively dissolved based on the pH condition so that the encasing 12 dissolves after the capsule 10 has passed through the highly acidic stomach and into the more neutral small intestine.

The elongate member 15 is preferably formed of a material that has elastic properties such as a Ni—Ti alloy, which permits it to be compressed into the initial configuration and to release into its elongate state when the encasing 12 has dissolved. As shown in FIG. 16, the elongate member 15 extends into its elongate form when the encasing 12 has dissolved.

The capsule body 11 is provided with a front portion 11a and a back portion 11b of reduced diameter. The encasing 12 is bonded to the back portion 11b by suitable means such as an adhesive. The diameter of the back portion 11b is reduced by a sufficient amount so that the thickness of the encasing 12 forms a substantially smooth outer capsule surface in conjunction with the outer surface of the front portion 11a of the capsule body 11. The overall conformation of the ingestible capsule 11 is cylindrical in shape having a generally hemispherical end surface 23 on the front portion 11a and a generally hemispherical end surface 24 on the back portion 11b. Dissolvable encasing 12 also has a generally hemispherical end surface 12a.

It is desirable that the elongate flexible member 15 have an extremity which has a curved configuration so as to ensure that the stimulation electrodes 16*a-c* are maintained in close proximity to the wall of the intestinal tract as the capsule 10 moves through the intestinal tract as hereinafter described. The electrode 17 is formed of a conducting layer of a suitable metal such as gold deposited on the surface of the capsule body 11. Alternatively, the additional electrodes 16*b* and 16*c* may be carried by additional elongate members constructed and secured to the capsule body 11 in a similar manner as elongate member 15.

The electronic circuitry 113 shown in FIG. 4 is capable of producing various types of programmable waveforms. FIGS. 17A and 17B illustrate examples of stimulation waveforms that may be used in stimulating the smooth muscle layer of the intestinal tract. FIG. 17A illustrates a waveform design for stimulating the intestinal tract. In a preferred embodiment, the waveform 300 has a pulse amplitude of between 1 and 30 mA, a pulse width of between 0.5 and 300 ms, and a frequency of about between 8 to 12 cycles per minute (this corresponds to a repetition period of between 5 to 7.5 seconds). FIG. 17B illustrates an alternative waveform design for stimulating the intestinal tract. The waveform 400 utilizes bursts of pulses rather than a single pulse. The burst repetition rate is selected, preferably, to be between about 8 to 12 cycles per minute (this corresponds to a burst repetition period of between 5 to 7.5 seconds). The duration of a pulse in this example is between about 300 .mu.s and 20 ms, and has an amplitude of about 1-30 mA. The frequency of the burst pulses during a burst period are about 50 to 100 Hz corresponding to a pulse repetition period of 10 to 20 ms. The burst duration can vary from about 0.6 ms to 1 second. As is well known to those skilled in the art, there are many different types of electrical stimulation programs and strategies which can be utilized for providing electrical stimulation parameters through the circuitry 113, the principal focus being providing electrically stimulating parameters for the intestinal tract, preferably the small intestine.

FIG. 18 illustrates a sixth embodiment of a capsule of the present invention. Stimulation capsule 50 is generally constructed in a similar manner as capsule 110. Capsule 50 comprises first bipolar electrode 56 and a second, electrically opposite bipolar electrode 57 on a capsule body 51 in longitudinally spaced apart positions. The electrodes 56, 57 are connected by conductors to the electronics 113 within the capsule body 51. According to this embodiment, various electrical stimulation parameters, including those described herein, may be used.

A seventh embodiment of the capsule is shown in FIGS. 19 and 20. Capsule 60 comprises a stimulation electrode deployment mechanism consisting of a loop 76 formed of an elastic material wrapped about the capsule body 61. Bipolar stimulating electrodes 66 and 67 are carried by the loop 76 and are connected to the electronic circuitry 113 in the capsule body 61 by conductors (not shown) extending through the hollow tubular member forming the loop 76. As shown in FIG. 19, a dissolvable encasing 62 is provided over the capsule body 61. This encasing 62 can be formed of the same material as the encasing 12 in the embodiment shown in FIG. 15. When encasing 62 is dissolved, the loop 76 will expand to the ovoid looped configuration shown in FIG. 20, bringing the stimulation electrodes 66 and 67 into contact with the wall of the intestinal tract as the capsule 60 travels through the intestinal tract. The loop 76 allows the electrodes 66, 67 to be positioned behind (orad to) the capsule 60 regardless of its orientation in the intestinal tract. As the capsule 60 moves through the intestinal tract the loop 76 will be in contact with the wall of the tract. The friction forces of the loop 76 dragging along the wall will cause the loop 76 to shift such that the electrodes 66, 67 are generally behind (orad to) the capsule. In this regard, a contraction stimulated by the electrodes 66, 67 will tend to result in forward (aborad) movement of the capsule as the stimulated contraction propagates along the intestinal tract.

FIGS. 21 and 22 illustrate an eighth embodiment of a capsule of the present invention. Capsule 80 includes an expandable member. In FIGS. 21 and 22, an inflatable member with pressure sensing capabilities is illustrated. Electronic circuitry 113 is located in the capsule body 81. A pressure transducer 127*a*, also located in the capsule body 81 is coupled to circuitry 113. The pressure transducer 127*a* comprises a commercially available silicone or other suitable plastic bridge pressure transducer that measures hydrostatic pressure to determine changes in pressures as described below.

An elongate member 85 is affixed to an end of the capsule body 81. Bipolar stimulation electrodes 86, 87 are located in a spaced apart relationship, rearwardly on the elongate member 85. Conductors 95 extend through the flexible elongate member 85 connecting the electrodes 86, 87 to the electronics 113. Opposing ends 92*a*, 92*b* of an inflatable balloon 92 are mounted forwardly of the electrodes 86, 87 on the flexible elongate tubular member 85 by a suitable adhesive (not shown). A balloon inflation/deflation lumen 94 is provided in the flexible elongate member 85 and extends from the capsule body 81 to an inflation port 93 that opens into the interior of the balloon 92 as shown in FIG. 22. The balloon inflation/deflation lumen 94 is coupled to the pressure transducer 127*a* so that compression pressures sensed by the balloon 92 will be supplied to the pressure transducer 127*a* as the pressure of the gas in the balloon 92 and the lumen 94 changes.

The capsule 80 includes a dissolvable encasing (not shown) of the same type as the encasing 12 shown in FIG. 15. Similar to the encasing shown in FIG. 15, such an encasing would enclose the flexible elongate member 85 including the inflatable balloon 92 and electrodes 86, 87 and would dissolve, e.g. in the small intestine releasing the elongate member 85 as illustrated in FIGS. 21 and 22.

A balloon inflator is provided within the capsule 80 comprising a small canister 97 of compressed $CO_2$ or other suitable gas. The canister 97 is coupled to the lumen 94 through a valve connection 98. The operation of the valve 98 is controlled by the electronics 113 through a driver 128*a, b, c,* or *d*. When the flexible elongate member 85 is deployed upon dissolving of the encasing, the electronics 113 cause the valve 98 to open and inflate the balloon 92.

Alternatively, the balloon 92 can be pre-inflated with a gas or fluid before enclosure within the encasing. In this case, the inflation canister 97 and valve 98 may be eliminated. The balloon 92 is formed of a gas impermeable material so that it will remain inflated over substantial periods of time. The balloon may be formed, for example, of polyurethane, PET, nylon or polyethylene.

In a preferred operation and use, the capsules shown in the various embodiments in FIGS. 12 and 18-22, are used in conjunction with the circuitry shown in FIG. 4 or FIG. 13 in small intestine electrical stimulation. A small intestine suited for treatment using the capsule may be diseased and incapable of adequate contractile activity. For example the nerves of the small intestine may be compromised due to gastric or diabetic neuropathy. Because of such a disorder, the patient may have a motility disorder that would be advantageously treated using small intestine electrical stimulation.

The stimulator capsule may also be used to measure other electrical characteristics such as EMG or impedance as described herein with respect to the electronic circuitry 113 show in FIG. 4. A patient wishing to treat a motility disorder ingests a capsule of the present invention near the beginning, midway, or following the ingestion of food. A capsule when ingested will travel through the esophagus into the stomach. Where a dissolvable encasing is utilized for encapsulating the elongate member and electrode(s), the encasing is readily dissolved by the fluids within the stomach or duodenum, permitting the flexible elongate member carrying the stimulation electrode to be deployed.

The capsule is preferably used with the tracking system described herein where treatment is triggered by an external (telemetry) signal from the tracking device. A first capsule may be delivered and an electrical parameter of the intestine may be mapped with respect to the length of the intestine. A second capsule may be delivered and used to provide electrical stimulation at an identified location along the length of the tract. An external signal to the capsule signals when to begin and end stimulation.

The electrical stimulation capsule may also be used independent of the tracking system. In a variation of the embodiment, the capsule can be programmed to begin emitting electrical stimuli to one or more stimulation electrodes 16a-c, and/or 17, within a predetermined time after ingestion, for example, within one to one and one-half hours after ingestion into the stomach, at which time it is most probable that the capsule would have passed into the duodenum along with food material passing from the stomach. As an alternative, a single capsule may stimulate and measure the electrical parameters. The capsule may sense electrical parameters and when a clinically undesirable electrical parameter is detected, the capsule may provide an appropriate electrical stimulation in. response.

Such a system would have the advantage of not requiring external gear such as the recorder and pods. Also, the capsule may be constructed to sense when it is in the duodenum, for example with a pH sensor or a pressure sensor. Also, the electronics 113 can be triggered to commence at the time the encasing is dissolved and the stimulation electrode is exposed to body fluids. Alternatively, electrical stimuli can be triggered by the electronics 113 to commence within a predetermined time after the encasing dissolves. In such case, the capsule is enclosed in a gel material that dissolves after it leaves the stomach when it reaches the small intestine. When triggered, electronic circuitry 113 initiates electrical stimuli to the small intestine of the patient, at periodic intervals, such as, for example using one or more waveforms like those shown in FIGS. 17A and 17B.

Alternative electronic circuitry 313 illustrated in FIG. 23 may be used with any of the stimulation capsules illustrated herein. According to an alternative embodiment, the electronic circuitry 313 is used in a simplified stimulation system. According to a preferred embodiment of the system, prior to each stimulation pulse or burst of pulses the capsule receives basic instructions. The instructions may be a trigger signal to trigger a stimulation pulse or burst of pulses with predetermined stimulation parameters, such as amplitude and pulse width, to be emitted by the capsule. The instructions may also include information regarding the stimulation parameters for the pulses to be emitted. The instructions to trigger and/or specify a stimulation pulse or burst of pulses to be delivered to the intestinal wall are telemetrically delivered to the electronic circuitry 313.

The electronic circuit 313 is simplified and includes a microprocessor 312, ROM 315, RAM 316, a clock 311, a telemetry coil 335, a battery 314 a dc-dc converter for stimulation 330, a telemetry detection circuit 317, and a pacing driver 318. The microprocessor 312 is coupled to the ROM 315, which contains program instructions for the microprocessor 312 and any other permanently stored information that allows the microprocessor 312 to operate. ROM 315 may also contain default and standard stimulation parameters. The microprocessor 312 addresses memory in a location in the ROM 315 through address bus 315a and the ROM 315 provides the stored program instructions to the microprocessor 312 via data bus 315b. The microprocessor is coupled to the RAM 316 via an address bus 316a for addressing a location in the RAM 316 and a bi-directional data bus 316b for delivering information to and from the RAM 316. The RAM 316 may be used by the microprocessor 312 to store custom stimulation parameters sent via telemetry prior to a series of stimulation pulses or bursts of pulses, or, just before each stimulation pulse or burst of pulses. RAM 316 may also temporarily store an identification code to specify the already stored default, standard or custom stimulation parameters to be used for stimulating the intestinal wall.

The trigger signals for each stimulating pulse or burst of pulses and the stimulation parameter instructions are supplied through the telemetry coil 335 to the microprocessor 312 and are then delivered through the pacing driver 318 in real time to the intestinal wall (through electrodes as described herein). Thus, the capsule itself does not direct the stimulation or the intestinal wall but receives directions from an external source and delivers stimulation accordingly and in real time to the intestinal wall.

The embodiment of FIG. 23 could be further simplified by replacing the microprocessor 312, ROM 315, RAM 316, and clock 311 with logic gates or a state machine. In such variation, some or all of the stimulation parameters may be preset and stored in the hardware in the capsule. For example, stimulation amplitudes could be stored as 5 different states in a simple state machine. The telemetry instruction signal could then consist of a simple pulse train that would represent the trigger signal as well as encode one of the five stimulation amplitudes while using an otherwise fixed stimulation pattern.

The electrical pulses provided by the electronics 113 through the electrode pairs 16a-c, 17 (as selected) (FIGS. 15, 16); 56, 57 (FIG. 18); 66, 67 (FIGS. 19, 20); 86, 87 (FIG. 21); and 116, 117 (FIG. 3A) may be used to create peristaltic contractions in the wall to cause movement of food material along with the capsule in the intestine. In an alternative embodiment where it is desired to retard motility in the small intestine, inhibition of peristaltic contractions by electrical stimulation may be effected by delivering electrical pulses designed to inhibit or interfere with the inherent electrical potentials, resulting in failure of normal peristaltic contractile activity.

In certain situations with respect to motility disorders, it may be desirable to supply synchronized stimulating pulses to the wall of the small intestine by the use of multiple pairs of stimulating electrodes such as, for example, a plurality of pairs similar to electrodes 16a-c carried on the flexible elongate tubular member secured to the capsule as shown in FIG. 12 and synchronizing the pulses in forward (aboard) or reverse (orad) directions in order to cause forward or reverse stimulation of the intestinal tract.

As the capsule passes along the intestinal tract, it continues to supply successive stimuli through the intestine. The rapidity of movement of food material through the small intestine can be controlled by the stimulating parameters such as frequency or amplitude of the signals utilized for supplying electrical stimuli or pulses to the intestinal tract. The capsule may provide certain stimulation patterns in the small intestine until it reaches the colon. (This may be determined by sensed electrical or other parameters, or by a predetermined time interval). At this time the electrical stimuli can be terminated or alternatively they can continue to be generated at the same or different parameters as the capsule passes through the colon until it exits from the body through the rectum in a bowel movement.

Where it is necessary for the patient to ingest a capsule each time food is ingested by the patient, the patient can have additional capsules on hand and ingest a capsule with each meal.

The electrode configuration preferably comprises two separate electrical elements forming electrically opposite bipolar electrodes. However, a monopolar or unipolar construction with a remote return is also contemplated by the invention. Spacing of the bipolar electrode elements from one another will preferably be about 5 mm. Electrodes formed on an elongate member will preferably be constructed from a metal wire or strip wound in a helical manner around the elongate tail portion. The electrode metal will preferably be corrosion resistant and biocompatible such as Gold, Platinum, Titanium, etc. A helical winding pattern is preferred to provide an electrode that is more flexible than a solid cylinder, and thereby allow the elongate tail to be more easily wound or compressed for containment in the dissolvable portion of the capsule. An alternative construction is contemplated where the electrode is embedded in an insulating polymer with an insulated lead extending within or along the elongate member into the capsule body.

By varying the spacing between the stimulation electrodes or the size of the electrodes, it is possible to change the current density passing through the wall of the intestine during stimulation. A device may be provided where electrodes may be selected to maximize these parameters. For example a plurality of electrode pairs may be provided from which the optimal pair of electrodes may be selected. Also individual electrodes may be configured to form a pair of bipolar electrodes upon selection.

The electrical pulses or pulse train supplied to the stimulation electrodes can be at suitable stimulation intervals as for example, in the case of pacing type electrical stimulation, every few seconds up to ten seconds in the small intestine or several hours in the colon.

In connection with the electrical stimulation functions described herein, it is often desirable to measure the pressures which are created by peristalsis of the intestinal contractions. Referring to FIGS. 21 and 22, this can be readily measured by sensing the compressive forces exerted on the balloon 92 with transducer 91. By sensing such pressures and supplying the information by telemetry to the external recorder 105, it is possible to ascertain the efficacy of the stimulation being applied to the particular portion of the intestinal tract and if necessary to adjust the electrical stimulation parameters to create the desired contractile forces being sensed by the balloon and the pressure transducer. For example, if the sensed pressure indicates suboptimal contractile response, the stimulation parameters may be adjusted, e.g., telemetrically. If the existence of contractions is detected, the stimulation electrodes may be turned off. This may also serve to conserve battery power.

One method of use of a capsule of the present invention is in small intestine electrical stimulation. Electronic circuitry is disposed within the capsule and creates electrical stimuli for causing peristaltic motion of the small intestine for causing pacing of peristaltic motion in the small intestine. Other effects on the electrical, chemical, and/or neural systems of the intestinal tract may be achieved with electrical stimulation. One example includes an electrical stimulus that is used to interfere with the natural pacesetter potential and thus prevent organized intestinal tract contractile activity from occurring.

The present invention provides an improved method and device for tracking an autonomous capsule as well as a method and device for tracking and diagnosing the gastrointestinal tract, preferably using a tracking device. Various modifications and combinations are contemplated by this invention and may be made without departing from the scope of the invention.

For example, in another embodiment of the tracking system, the direction of the ultrasound signal used for locating the capsule is reversed. In this embodiment, the capsule receives the ultrasound signals generated by the pods and retransmits the signals on the RF carrier back to the pods or external monitor. In this way, the capsule position may be located by measuring the time delay from transmission of the ultrasound signal(s) by the pod(s) to their reception by the capsule. Rather than activating all pods simultaneously, each pod may be sequentially activated to transmit ultrasound. Accordingly, the pod to capsule path is identified by the time of transmission from a particular pod. When a single pod is activated in this way for transmission, all the remaining pods may also be switched to receive the ultrasound signal from the transmitting pod. This allows the pod-to-pod delay times to be measured, so that the relative position of the pods can be determined on an ongoing basis.

If simultaneous transmission from all pods is desired, the ultrasound signals from each pod may be separated by using a variety of methods. For example, each pod may generate a unique ultrasound frequency allowing the signals to be separated by filtering.

In one variation, for example, a continuous wave signal with amplitude modulation may be used rather than a narrower pulse. In such variation, time delays may be measured by measuring the phase of the received signals relative to the transmitted signal.

Alternative reference signals may be used to establish when the acoustic signal is transmitted. For example, an infra-red link or a distributed resistive link may be used. Infra-red links may be constructed using light emitting diodes with an infra-red wavelength chosen to minimized the effects of tissue/light attenuation. The light transmitters and sensors may be on the capsule and/or at the external location for one or two way signal transmission. The light may be modulated with a high frequency carrier in a similar manner to an RF link. The modulated light signal can then be detected after it has passed through the tissue using a light sensor or sensors. A distributed resistive link may be used to directly couple an electrical carrier signal through the body to an external sensor or sensors, or alternatively or additionally from an external transmitter to electrode sensors coupled to the capsule. A small high frequency carrier, typically 100 kHz or above, is preferably chosen for the carrier frequency to prevent any muscle stimulation by the carrier. The sensor on the capsule or at the external location would then detect the high frequency carrier signal, which would be attenuated by the distributed resistive divider formed by the conductive body tissue. To transmit or receive the signal to or from an external location, the external source or sensor would be coupled into the body via two skin electrodes, spaced at some distance apart. Electrodes on the capsule would be used to receive (or transmit) such carrier signal. The high frequency carrier would preferably be modulated in the same way as an RF link, using amplitude, frequency or other modulation schemes as are well known in the art. Preferably, the various signals e.g., going to or from the capsule, would be placed on different carrier frequencies to allow for easy separation via filtering, of the outgoing and incoming signals.

Further, as an alternative to using an externally detectable signal such as an RF signal, as a reference signal to establish the time at which the acoustic pulse is emitted, the ultrasound transmitters and receivers may be configured to establish such transmission times and thus the location of the capsule. Based on the differential time between two ultrasound receivers receiving an ultrasound pulse from a capsule, the possible location of the capsule may be defined by a paraboloid plane between the two receivers. Using more than two receivers, additional such paraboloid planes representing possible locations may be determined. The intersection of the planes provides information from which the actual location of the capsule may be derived. By filtering out impossible locations (e.g., by knowing points that would lie outside a patient's body, e.g., based on pod placement on a patient, or by adding additional pods for additional location information), the actual location of the capsule may be determined.

According to one variation, the differential distance is determined by multiplying the differential time between the reception of the ultrasound signal at one pod and the reception at the other pod times the speed of sound in tissue. The possible location of the capsule based on the derived differential distance is represented by a paraboloid plane between the two pods. When a third acoustic reference receiver is added, the detected differential time between receiver one and three and the differential time between receivers two and three provide additional paraboloid planes of possible capsule locations. Two paraboloid planes intersect in a paraboloid or ellipsoid line; intersection with a third paraboloid plane defines one or more points of possible capsule locations. Strategic positioning of the acoustic reference receivers, use of additional receivers and/or exclusion of invalid mathematical solutions (e.g. outside of the patient's body) may enable a single solution to be obtained for capsule location.

The foregoing embodiments and variations of the invention are illustrative and not contemplated to be limiting, having been presented by way of example. Numerous other variations and embodiments, as would be apparent to one of ordinary skill in the art, are contemplated as falling within the scope of the invention as defined by the claims and equivalents thereof.

The invention claimed is:

1. A system for the delivery of a drug to a gastrointestinal tract, the system comprising:
   a capsule sized to pass through an intestinal tract of a patient;
   a transmitter coupled to the capsule, the transmitter configured to transmit a tracking signal between the capsule and a location external to a patient's body to track a linear position of the capsule within the patient's intestinal tract as the capsule is passing through the intestinal tract;
   a reference signal generator coupled to the capsule, the reference signal generator configured to generate and transmit a reference signal for identifying a time of tracking signal origination;
   a drug delivery device configured to deliver drug to the intestinal tract; and
   a controller configured to actuate the drug delivery device as the capsule is passing through the intestinal tract at a desired position in the intestinal tract based on the capsule position within the intestinal tract.

2. The system of claim 1 wherein the drug delivery device comprises a pump.

3. The system of claim 1, wherein the drug delivery device comprises a valve or a solenoid.

4. The system of claim 1, wherein the controller is actuable responsive to an external signal.

5. The system of claim 4, wherein the drug delivery device includes an RF receiver for receiving the external signal, the RF receiver operably coupled to at least one of the controller or the drug delivery device.

6. The system of claim 4, wherein the controller actuates the drug delivery device responsive to the external signal.

7. The system of claim 6, wherein the controller includes programming for actuating the drug delivery device responsive to the external signal.

8. The system of claim 1, further comprising:
   a sensor for sensing a condition of the intestinal tract, the sensor operably coupled to at least one of the controller or the drug delivery device.

9. The system of claim 8, wherein the sensor comprises a pressure sensor, a strain gauge or a pH sensor.

10. The system of claim 8, wherein the drug delivery device is actuatable responsive to the sensed condition of the intestinal tract.

11. The system of claim 10, wherein the controller actuates the drug delivery device responsive to the sensed condition of the intestinal tract.

12. The system of claim 11, wherein the controller includes programming for actuating the drug delivery device responsive to the sensed condition.

13. The system of claim 1, wherein the capsule includes the drug.

14. The system of claim 1 further comprising:
   a plurality of transducers configured to receive the tracking signal.

15. The system of claim 14, wherein the plurality of transducers comprises at least three transducers.

16. The system of claim 14, wherein the plurality of transducers are acoustic transducers and the tracking signal is an acoustic tracking signal.

17. The system of claim 14, wherein the plurality of transducers are configured to receive and transmit signals between each other.

18. The system of claim 14, wherein the plurality of transducers are adhereably positioned on the patient's skin.

19. The system of claim 14, wherein at least one of the plurality of transducers also includes an RF device for receiving and/or sending signals to the capsule.

20. The system of claim 14, further comprising:
   a patient wearable recorder device coupled to the plurality of transducers, the recorder device configured to record output from the plurality of transducers.

21. A system for the delivery of a drug to a gastrointestinal tract, the system comprising:
   a stimulation capsule including a plurality of electrodes; wherein the order in which a series of electrode pairs are activated causes peristalsis to move in a directional manner;
   the stimulation capsule sized to pass through an intestinal tract of a patient;
   a transmitter coupled to the capsule, the transmitter configured to transmit a tracking signal between the capsule and a location external to a patient's body to track a linear position of the capsule within the patient's intestinal tract as the capsule is passing through the intestinal tract;

a reference signal generator coupled to the capsule, the reference signal generator configured to generate and transmit a reference signal for identifying a time of tracking signal origination;

a drug delivery device configured to deliver drug to the intestinal tract; and a controller configured to actuate the drug delivery device as the capsule is passing through the intestinal tract at a desired position in the intestinal tract based on the capsule position within the intestinal tract.

* * * * *